(12) United States Patent
Pieken et al.

(10) Patent No.: US 6,737,236 B1
(45) Date of Patent: May 18, 2004

(54) BIOCONJUGATION OF MACROMOLECULES

(75) Inventors: Wolfgang Pieken, Boulder, CO (US); Ken Hill, Nederland, CO (US); Bruce Eaton, Boulder, CO (US); Danny McGee, San Mateo, CA (US); Kurt Vagle, Longmont, CO (US); Larry Gold, Boulder, CO (US); Andrew Stephens, Boulder, CO (US)

(73) Assignee: Proligo, LLC, Boulder, CO (US)

( * ) Notice: Subject to any disclaimer, the term of this patent is extended or adjusted under 35 U.S.C. 154(b) by 0 days.

(21) Appl. No.: 09/341,337

(22) PCT Filed: Jan. 8, 1998

(86) PCT No.: PCT/US98/00649
§ 371 (c)(1),
(2), (4) Date: Jul. 8, 1999

(87) PCT Pub. No.: WO98/30575
PCT Pub. Date: Jul. 16, 1998

Related U.S. Application Data

(63) Continuation-in-part of application No. 09/051,449, filed on Apr. 6, 1998, now Pat. No. 6,262,251, and a continuation-in-part of application No. 08/780,517, filed on Jan. 8, 1997, now Pat. No. 5,874,532.

(60) Provisional application No. 60/034,651, filed on Jan. 8, 1997, and provisional application No. 60/058,206, filed on Sep. 8, 1997.

(51) Int. Cl.[7] .......................... C12Q 1/68; C07H 21/02; C07H 19/00

(52) U.S. Cl. .................... 435/6; 435/174; 568/767; 424/193.1; 534/766; 536/22.1; 530/350

(58) Field of Search ............... 568/767; 424/193.1; 534/766; 536/22.1; 530/350; 435/174, 6

(56) References Cited

U.S. PATENT DOCUMENTS

| | | |
|---|---|---|
| 4,291,024 A | 9/1981 | Turcotte |
| 4,616,071 A * | 10/1986 | Holubka et al. ............ 525/524 |
| 5,093,232 A | 3/1992 | Urdea et al. |
| 5,118,800 A | 6/1992 | Smith et al. |
| 5,118,802 A | 6/1992 | Smith et al. |
| 5,200,514 A | 4/1993 | Chu |
| 5,420,276 A | 5/1995 | Norbeck |
| 5,466,786 A | 11/1995 | Buhr et al. |
| 5,539,082 A | 7/1996 | Nielsen et al. ............ 530/300 |
| 5,576,429 A | 11/1996 | Johansson et al. |
| 5,580,697 A * | 12/1996 | Keana et al. ............ 430/296 |
| 5,874,532 A * | 2/1999 | Pieken et al. ............ 530/338 |
| 6,090,932 A | 7/2000 | McGee et al. |

FOREIGN PATENT DOCUMENTS

| | | |
|---|---|---|
| DE | 25 31 257 | 1/1976 |
| EP | 2931233 | * 2/1981 |
| EP | 0 453 247 A2 | 10/1991 |
| WO | WO 91/06556 | 5/1991 |
| WO | WO 91/10671 | 7/1991 |
| WO | WO 91/13900 | 9/1991 |
| WO | WO 94/13789 | 6/1994 |
| WO | WO 95/24185 | 9/1995 |
| WO | WO 96/34984 | * 11/1996 |

OTHER PUBLICATIONS

Aurup et al. (1992) Biochemistry 31:9636–9641.
Englisch and Gauss (1991) Angew. Chem. Int. Ed. Engl. 30:613–627.
Huryn and Okabe (1992) Chemical Reviews 92:1745–1768.
Ludwig and Eckstein (1989) J. Org. Chem. 54:631–635.
Mikhailopulo et al., (1993) Liebigs Ann. Chem. pp. 513–519.

(List continued on next page.)

Primary Examiner—Jezia Riley
(74) Attorney, Agent, or Firm—Swanson &Bratschun, L.L.C.

(57) ABSTRACT

This invention discloses a novel method for conjugating macromolecules to other molecular entities. Specifically, this invention discloses a method for conjugating or derivatizing macromolecules, such as oligonucleotides and proteins, using cycloaddition reactions, such as the Diels-Alder reaction or 1,3-dipolar cycloadditions. Included in the invention are the novel bioconjugated macromolecules that can be prepared according to the method of the invention.

19 Claims, 5 Drawing Sheets

OTHER PUBLICATIONS

Nishikubo et al. (1981) Tetrahedron Letters 22:3873–3874.
Roush et al. (1983) Tetrahedron Letters 24:1377–1380.
Shibuya and Ueda (1980) Chem. Pharm. Bull. 28:939–946.
Schmidt (1994) Synlett 4:241–242.
Tronchet et al. (1990) Tetrahedron Letters 31:531–534.
Tronchet et al. (1988) Nucleosides & Nucleotides 7:249–269.
Verheyden et al. (1971) J. Org. Chem. 36:250–254.
Wagner et al. (1991) Nucleic Acids Res. 19:5965–5971.
Warshaw et al. (1990) J. Med. Chem. 33:1663–1666.
Giuliano et al. Journal of Organic Chemistry, 1990, 55, 3555–3562.*
Jager et al. Tetrahedron Letters, vol. 36, No. 6, 861–854, 1995.*
Lubineau et al. Carbohydrate Research 270, 163–179, 1995.*
Giuliano et al. Journal of Organic Chemistry, 1993, 58, 4979–4988.*
Bruick et al. (1996) Chemistry & Biology 3:49–56.
Bruick et al. (1997) Nucleic Acids Res. 25:1309–1310.
Eritja et al. (1991) Tetrahedron 47: 4113–4120.
Goodchild (1990) Bioconjugate Chemisry 1:165–187.
Haralambidis et al. (1990) Nucleic Acids Res. 18:493–499.
Haralambidis et al. (1987) Tetrahedron Lett. 28:5199–5202.
Jones et al. (1995) J. Med. Chem. 38:2138–2144.
Juby et al. (1991) Tetrahedron Lett. 32:879–882.
Krieg et al. (1991) Antisense Res. and Dev.1:161–171.
Leonetti et al. (1990) Bioconjugate Chem. 1:149–153.
Mori et al. (1989) Nucleosides & Nucleotides 8:649–657.
Sinha and Cook (1988) Nucleic Acids Res. 16:2659–2669.
Smith et al. (1987) Methods in Enzymology, 155:260–301.
Sproat et al. (1987) Nucleic Acids Research 15:6181–6196.
Theisoen et al. (1992) Tetrahedron Lett. 33:5033–5036.
Zalipsky (1995) Bioconjugate Chem. 6:150–165.
Tung (1991) Bioconjugate Chem. 2:464–465.

* cited by examiner

SEQUENCE LISTING

```
<160> NUMBER OF SEQ ID NOS:  1

<210> SEQ ID NO 1
<211> LENGTH: 28
<212> TYPE: DNA
<213> ORGANISM: Artificial Sequence
<220> FEATURE:
<221> NAME/KEY: modified_base
<222> LOCATION: (1)..(28)
<223> OTHER INFORMATION: Linkage  at positions 27 and 28 is 3'-3'.
<223> OTHER INFORMATION: Description of Artificial Sequence:  Synthetic
      Sequence

<400> SEQUENCE: 1
ccagtacaag gtgctaaacg taatggtt                                             28
```

BIOCONJUGATION OF MACROMOLECULES

CROSS REFERENCE TO RELATED APPLICATIONS

This application is a 371 of International Application Number PCT/US98/00649, filed Jan. 8, 1998 (Publication No. WO 98/30575), entitled "Bioconjugation of Macromolecules," which claims the benefit of U.S. Provisional Application Serial No. 60/034,651, filed Jan. 8, 1997 and U.S. Provisional Application Serial No. 60/058,206, filed Sep. 8, 1997. This application is also a continuation in part of application Ser. No. 09/051,449, filed Apr. 6, 1998, now U.S. Pat. No. 6,262,251, issued Jul. 17, 2001, entitled "Method for Solution Phase Synthesis of Oligonucleotides," and application Ser. No. 08/780,517, filed Jan. 8, 1997, now U.S. Pat. No. 5,874,532, issued Feb. 23, 1999, entitled "Method for the Solution Phase Synthesis of Oligonucleotides and Peptides."

FIELD OF THE INVENTION

This invention describes a novel method for conjugating macromolecules to other molecular entities. Particularly, this invention describes a method for conjugating or derivatizing oligonucleotides and proteins using cycloaddition reactions, such as the Diels-Alder reaction or 1,3-dipolar cycloaddition reactions.

BACKGROUND OF THE INVENTION

A method for the in vitro evolution of nucleic acid molecules with highly specific binding to target molecules has been developed. This method, Systematic Evolution of Ligands by Exponential Enrichment, termed SELEX, is described in U.S. patent application Ser. No. 07/536,428, filed Jun. 11, 1990, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Methods for Identifying Nucleic Acid Ligands," now U.S. Pat. No. 5,270,163 (see also WO 91/19813), each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as nucleic acid ligands (also referred to in the art as "aptamers"), each ligand having a unique sequence and property of binding specifically to a desired target compound or molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," abandoned in favor of U.S. patent application Ser. No. 08/198,670, describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting nucleic acid ligands containing photoreactive groups capable of binding and/or photocrosslinking and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443,957, now U.S. Pat. No. 5,580,737, describes a method for identifying highly specific nucleic acid ligands able to discriminate between closely related molecules, which can be non-peptidic, termed Counter-SELEX. U.S. patent application Ser. No. 08/143,564, filed Oct. 5, 1993, entitled "Systematic Evolution of Ligands by Exponential Enrichment: Solution SELEX," abandoned in favor of U.S. patent application Ser. No. 08/461,069, now U.S. Pat. No. 5,567,588, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 09/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459 and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method encompasses complexes of oligonucleotides. U.S. patent application Ser. No. 08/434,465, filed May 4, 1995 entitled "Nucleic Acid Ligand Complexes," describes a method for preparing a therapeutic or diagnostic complex comprised of a nucleic acid ligand and a lipophilic compound or a non-immunogenic, high molecular weight compound.

Nucleic acid ligands derived by the SELEX process have been used in diagnostic applications. (See e.g., U.S. patent application Ser. No. 08/487,425, filed Jun. 7, 1995, entitled "Enzyme Linked Oligonucleotide Assays (ELONAS)," U.S. patent application Ser. No. 08/479,729, filed Jun. 7, 1995, entitled "Use of Nucleic Acid Ligands in Flow Cytometry," and U.S. patent application Ser. No. 08/628,356, filed Apr. 5, 1996, entitled "Method for Detecting a Target Compound in a Substance Using a Nucleic Acid Ligand." The full text of the above described patent applications, including but not limited to, all definitions and descriptions of the SELEX process, are specifically incorporated by reference herein in their entirety.

Considerable research is being directed to the application of oligonucleotides and oligonucleotide analogs as diagnostic and research reagents and as potential therapeutic agents. There are currently at least three areas of exploration regarding the use of oligonucleotides as pharmaceutical compounds. In the most advanced field, antisense oligonucleotides are used to bind to certain coding regions in an organism to prevent the expression of proteins or to block various cell functions. Additionally, the discovery of RNA species with catalytic functions—ribozymes—has led to the study of RNA species that serve to perform intracellular reactions that will achieve desired effects. And lastly, the discovery of the SELEX process (Systematic Evolution of Ligands by Exponential Enrichment) (Tuerk and Gold (1990) Science 249:505) has shown that oligonucleotides can be identified that will bind to almost any biologically interesting target.

The use of antisense oligonucleotides as a means for controlling gene expression and the potential for using oligonucleotides as possible pharmaceutical agents has prompted investigations into the introduction of a number of chemical modifications into oligonucleotides to increase their therapeutic activity and stability. Such modifications are designed to increase cell penetration of the oligonucleotides, to stabilize them from nucleases and other enzymes that degrade or interfere with the structure or activity of the oligonucleotide analogs in the body, to enhance their binding to targeted RNA, to provide a mode of disruption (terminating event) once sequence-specifically bound to targeted RNA and to improve the pharmacokinetic properties of the oligonucleotides.

Recent research has shown that RNA secondary and tertiary structures can have important biological functions (Tinoco et al. (1987) Cold Spring Harb. Symp. Quant. Biol. 52:135; Larson et al. (1987) Mol. Cell. Biochem. 74:5; Tuerk et al. (1988) Proc. Natl. Acad. Sci. USA 85:1364; Resnekov et al. (1989) J. Biol. Chem. 264:9953). PCT Patent Application Publication WO 91/14436, entitled "Reagents and Methods for Modulating Gene Expression Through RNA Mimicry," describes oligonucleotides or oligonucleotide analogs which mimic a portion of RNA able to interact with one or more proteins. The oligonucleotides contain modified internucleoside linkages rendering them nuclease-resistant, have enhanced ability to penetrate cells, and are capable of binding target oligonucleotide sequences.

The use of oligonucleotides as therapeutic and diagnostic agents is growing rapidly with many compounds in human clinical trials. In many of these applications the oligonucleotide is derivatized or conjugated with another molecular entity. These conjugations are typically performed for the purpose of attaching fluorescent dyes or other diagnostic reporter groups or for attaching compounds that modulate the activity or the pharmacokinetic behavior of the oligonucleotide. For example, Smith et al. describe the synthesis of fluorescent dye-conjugated primers for use in fluorescence-based DNA sequence analysis (Smith et al. (1987) Methods Enzymol. 155: 260–301). U.S. Pat. No. 5,650,275 of Pitner et al., describes the use of spectroscopically detectable labeled nucleic acid ligands to determine the presence or absence of a target compound in a sample (see also copending U.S. patent application No. 08/487,425, filed Jun. 7, 1995, entitled "Enzyme Linked Oligonucleotide Assays (ELONAS)," U.S. patent application No. 08/479,729, filed Jun. 7, 1995, entitled "Use of Nucleic Acid Ligands in Flow Cytometry," and U.S. patent application No. 08/628,356, filed Apr. 5, 1996, entitled "Method for Detecting a Target Compound in a Substance Using a Nucleic Acid Ligand"). U.S. patent application Ser. No. 08/434,465, filed May 4, 1995, entitled "Nucleic Acid Ligand Complexes," describes the use of oligonucleotides conjugated to lipophilic compounds or non-immunogenic, high molecular weight compounds to modulate the activity or pharmokinetic behavior of the oligonucleotides. Conjugation has also been used to make oligonucleotide dimers and to attach oligonucleotides to multimeric platforms. (Jones et al. (1995) J. Med. Chem. 38:2138).

Several chemical methods exist to accomplish such conjugations. (For a review, see Goodchild (1990) Bioconjugate Chemistry 1:165–187). The presence of a chemically reactive functional group, such as an amine or thiol, at the 5'-terminus of an oligonucleotide allows selective attachment of various conjugates, including reporter groups (Smith et al. (1987) Methods Enzymol. 155:260–301; Sproat et al. (1987) Nucleic Acids Res. 15:6181–6196; Mori et al. (1989) Nucleosides & Nucleotides 8:649; Sinha et al. (1988) Nucleic Acids Res. 16:2659) and peptide epitopes (Tung et al. (1991) Bioconjugate Chem. 2:464–465; Bruick et al. (1996) Chem. Biol. 3:49–56). Oligodeoxynucleotides containing a terminal amino functionality have been utilized for the construction of bioconjugates with novel properties. In some of the more common methods of synthesizing these bioconjugates, a primary, aliphatic amino group is incorporated at the 5'-terminus of the oligonucleotide in the final step of the assembly of a synthetic oligonucleotide (Tung et al. (1991) Bioconjugate Chem. 2:464–465; Smith et al. (1987) Methods Enzymol. 155:260–301). A commercial reagent (actually a series of such linkers having various lengths of polymethylene connectors) for linking to the 5' terminus of an oligonucleotide is 5'-Amino-Modifier C6. These reagents are available from Glen Research Corp (Sterling, Va.). These compounds have been used by Krieg (Krieg et al. (1971) Antisense Res. and Dev.1:161) to link fluorescein to the 5'-terminus of an oligonucleotide. Since many macromolecules of interest are hydrophilic, these reactions generally are done in water, requiring large excesses of reagent to overcome the competing hydrolysis. Usually the amine on the oligonucleotide is added to the terminus of the molecule and must compete with free amine and alcohol on the fully deprotected oligonucleotide if this modification is done post-synthetically.

In another common method of conjugating oligonucleotides to other molecular entities, particularly detector molecules, the molecular entity is converted into a phosphoramidite, which is then added to the free alcohol of the full length oligonucleotide which is attached to a solid support (Theison et al. (1992) Tetrahedron Lett. 33:5033–5036). This method is less than ideal due to the air and water sensitivity of the phosphoramidite, as well as, the fact that the molecule can only be added to the terminus of the oligonucleotide. Furthermore, many detector molecules are not compatible with this method due to the harsh conditions normally needed to fully deprotect and release the oligonucleotide from the support. A third method of conjugating oligonucleotides to other molecules is the coupling of an alkylthio derivatized oligonucleotide with a α-haloacetyl or with a maleimide containing compound. (Jones et al. (1995) J. Med. Chem. 38:2138).

An alternative method for the synthesis of oligodeoxynucleotides terminated by 5'-amino-5'-deoxythymidine has been described (Bruick et al. (1997) Nucleic Acids Res. 25:1309–1310). This method uses a DNA template to direct the ligation of a peptide to an oligonucleotide, in which the peptide is presented by a second oligonucleotide in the form of a reactive thioester-linked intermediate.

The preparation of PEG-oligonucleotide conjugates is described by Goodchild (1990) Bioconjugate Chem. 1:165 and Zalipsky (1995) Bioconjugate Chem. 6:150). The preferred solvent for macromolecule conjugation reactions is an aqueous buffer. Most conjugation chemistry methods must be carried out at high pH and therefore, suffer severely from competing hydrolysis reactions. In addition, most conjugation reactions display poor chemoselectivity.

The preparation of conjugates of macromolecules is not limited to oligonucleotide conjugates. Proteins and peptides play a critical role in virtually all biological processes, functioning as enzymes, hormones, antibodies, growth factors, ion carriers, antibiotics, toxins, and neuropeptides. Proteins and peptides comprise a prominent class of pharmaceuticals. Conjugation of proteins and peptides to detector molecules or other macromolecules such as PEG is also a common practice. Conjugates of oligonucleotides with peptides having specific functions can be useful for various applications. Examples include the use of a nuclear transport signal peptide to direct intracellular trafficking (Eritja et al. (1991) Tetrahedron 47: 4113–4120); a hydrophobic peptide (Juby et al. (1991) Tetrahedron Lett. 32:879–822) or polylysine (Leonetti et al. (1991) Bioconjugate Chem. 1:149–153) to increase cell penetrability, and polylysine to provide multiple attachment sites for nonradioactive reporting probes (Haralambidis et al. (1987) Tetrahedron Lett. 28:5199–5202; Haralambidis et al. (1990) Nucleic Acids Res. 18:493–499).

Cycloaddition reactions can be defined as any reaction between two (or more) moieties (either intra or intermolecular) where the orbitals of the reacting atoms form a cyclic array as the reaction progresses (typically in a concerted fashion although intermediates may be involved) along the reaction coordinate leading to a product. The orbitals involved in this class of reactions are typically $\pi$ systems although certain $\sigma$ orbitals can also be involved. The number of electrons associated with this type of reaction are of two types; 4n+2 and 4n, were n=1, 2, 3, 4 etc. Typical examples of cycloaddition reactions include Diels-Alder cycloaddition reactions, 1,3-dipolar cycloadditions and [2+2] cycloadditions.

The Diels-Alder reaction, by far the most studied cycloaddition, is a cycloaddition reaction between a conjugated diene and an unsaturated molecule to form a cyclic compound with the $\pi$-electrons being used to form the new $\sigma$ bonds. The Diels-Alder reaction is an example of a [4+2] cycloaddition reaction, as it involves a system of 4-$\pi$ electrons (the diene) and a system of 2-$\pi$ electrons (the dienophile). The reaction can be made to occur very rapidly, under mild conditions, and for a wide variety of reactants. The Diels-Alder reaction is broad in scope and is well known to those knowledgeable in the art. A review of the Diels-Alder reaction can be found in "Advanced Organic Chemistry" (March. J., ed.) 761–798 (1977) McGraw Hill, N.Y., which is incorporated herein by reference.

It has been discovered that the rate of Diels-Alder cycloaddition reactions is enhanced in aqueous solvents. (Rideout and Breslow (1980) J. Am. Chem. Soc. 102:7816). (A similar effect is also seen with 1,3-dipolar cycloaddition reactions (Engberts (1995) Tetrahedron Lett. 36:5389). This enhancement is presumably due to the hydrophobicity of the diene and dienophile reactants. (Breslow (1991) Acc. Chem. Res. 24:159). This effect extends to intramolecular Diels-Alder reactions. (Blokzijl et al. (1991) J. Am. Chem. Soc. 113:4241). Not only is the reaction rate accelerated in water, but several examples of an increased endo/exo product ratio are also reported. (Breslow and Maitra (1984) Tetrahedron Lett. 25:1239: Lubineau et al. (1990) J. Chem. Soc. Perkin Trans. I, 3011; Grieco et al. (1983) Tetrahedron Lett. 24:1897). Salts which increase the hydrophobic effect in water, such as lithium chloride (Breslow et al. (1983) Tetrahedron Lett. 24:1901) and also monovalent phosphates (Pai and Smith (1995) J. Org. Chem. 60:3731) have been observed to further accelerate the rate of 4+2 cycloadditions.

The synthetic potential of the Diels-Alder reaction in aqueous solvents is gaining increasing attention. It has been demonstrated that simple dienes, such as sodium 3,5-hexadienoate and sodium 4,6-heptadienoate readily undergo Diels-Alder reactions in water with a variety of dienophiles at ambient temperature. (Grieco et al. (1983) J. Org. Chem. 48:3137). The otherwise difficult cycloaddition of dimethyl acetylenedicarboxylate to an electron deficient furan proceeds under very mild conditions in water with very good yields. (Saksena et al. (1993) Heterocycles 35:129). The scope of the reaction has been extended to cycloaddition of iminium salts, generated in situ from an ammonium salt and formaldehyde to dienes. (Grieco and Larsen (1985) J. Am. Chem. Soc. 107:1768). This work inspired the exploration of the corresponding reaction of iminium salts of amino acids with dienes which proceeds with high stereoselectivity. (Grieco et al. (1986) Tetrahedron Lett. 27:1975; Grieco and Bahsas (1987) J. Org. Chem. 52:5745; Waldmann (1989) Liebigs Ann. Chem., 231–238; Waldmann and Braun (1991) Liebigs Ann. Chem., 1045–1048). The scope of this reaction has also been extended to more complex aldehydes by use of lanthanide(III) trifluoromethanesulfonates as catalysts. (Yu et al. (1996) Tetrahedron Lett. 37:2169).

In copending PCT Application Serial No. PCT/US96/16668, filed on Oct. 17, 1996, designating the United States, entitled "Method for Solution Phase Synthesis of Oligonucleotides" and U.S. application Ser. No. 08/843,820 entitled "Method for Solution Phase Synthesis of Oligonucleotides," both of which are incorporated herein by reference in their entirety, the Diels-Alder cycloaddition reaction is shown to be an ideal method for anchoring oligonucleotides onto resins. Resins derivatized with a diene or dienophile are reacted with an oligonucleotide derivatized with a dienophile or diene, respectively, to yield the Diels-Alder cycloaddition product. In particular, Diels-Alder reactions between oligonucleotides derivatized with a diene and polymeric resins derivatized with maleimide groups and with phenyl-triazoline-diones (PTAD) are described. The resulting resins can be used as affinity chromatography resins.

The present invention illustrates that cycloaddition reactions, such as the Diels-Alder reaction and 1,3-dipolar cycloaddition reactions, are an ideal replacement for current methods of conjugating macromolecules with other molecular moieties. The Diels-Alder reaction, in particular, is an ideal method for covalently linking large water soluble macromolecules with other compounds as the reaction rate is accelerated in water and can be run at neutral pH. (Rideout and Breslow (1980) J. Am. Chem. Soc. 102:7816). Additionally, the nature of the reaction allows post-synthetic modification of the hydrophilic macromolecule without excess reagent or hydrolysis of the reagent. With respect to conjugation to oligonucleotides, this technology has been aided by the ability to efficiently synthesize 2'-O-dienenucleosides, which allows the conjugation site to be varied throughout the oligonucleotide or the option of having multiple conjugation sites.

BRIEF SUMMARY OF THE INVENTION

The present invention describes a novel, chemoselective and highly efficient method for derivatizing or conjugating macromolecules with other molecular entities. Specifically, the present invention describes the use of cycloaddition reactions, including but not limited to Diels-Alder reactions, 1,3-dipolar cycloaddition reactions and [2+2] cycloaddition reactions, for the chemoselective and efficient derivatization or conjugation of macromolecules with other molecular entities. Thus, a macromolecule bearing a moiety capable of undergoing a cycloaddition reaction, is reacted with another molecular entity bearing a moiety capable of undergoing a cycloaddition reaction with the moiety attached to the macromolecule to yield via a cycloaddition reaction efficient conjugation of the molecular entity to the macromolecule.

In a preferred embodiment the cycloaddition reaction is a Diels-Alder reaction. Thus, a macromolecule bearing either a diene or dienophile moiety is reacted with another molecular entity bearing either a dienophile or a diene moiety, respectively, to yield via a cycloaddition reaction efficient conjugation of the molecular entity to the macromolecule.

In one embodiment the macromolecule is an oligonucleotide. Thus, an oligonucleotide bearing either a diene modified nucleoside or non-nucleoside phosphate diester group, or a dienophile modified nucleoside or non-nucleoside phosphate diester group is reacted with a molecular entity bearing either a dienophile or a diene moiety. Diels-Alder cycloaddition leads to efficient conjugation of the oligonucleotide with the molecular entity. The molecular entity can be any molecule, including another macromolecule which can be derivatized with a dienophile, diene or other moiety capable of undergoing a cycloaddition reaction. Examples of molecular entities include but are not limited to other macromolecules, polymers or resins, such as polyethylene glycol (PEG) or polystyrene, diagnostic detector molecules, such as fluorescein, coumarin or a metal chelator.

The Diels-Alder cycloaddition between a diene modified oligonucleotide and a dienophile modified oligonucleotide (or any cycloaddition reaction between suitably derivatized oligonucleotides and their reacting partners) results in efficient and specific formation of oligonucleotide homo-dimers and hetero-dimers. In addition, dimers or multimers of oligonucleotides can be prepared efficiently by reaction of two or more diene-modified oligonucleotides with a linker group bearing two or more dienophile moieties. Conventional activated acid linking chemistries do not allow for efficient dimerization or multimerization, since they are limited by competing hydrolysis of the activated acid reagents by water.

This invention includes a reaction scheme for producing a wide variety of conjugated macromolecules using cycloaddition reactions as typified by the Diels-Alder cycloaddition reaction and 1,3-dipolar cycloaddition reactions. The method of this invention can be extended to the conjugation of any macromolecule with another molecular entity, including but not limited to nucleic acids, proteins, peptides carbohydrates, polysaccharides, glycoproteins, lipids, hormones, drugs or prodrugs.

The method of this invention can be extended to all 4n and 4n+2 cycloadditions (where n=1, 2, 3, 4, etc.). This includes, but is not limited to Diels-Alder cycloadditions, 1,3-dipolar cycloadditions, ene cycloaddition reactions, and [2+2] (a 4n type) cycloadditons such as ketene additions and photochemical 2+2 additions.

Also included in this invention are any novel conjugated macromolecules produced by the method of this invention.

DETAILED DESCRIPTION OF THE INVENTION

Figure 1:
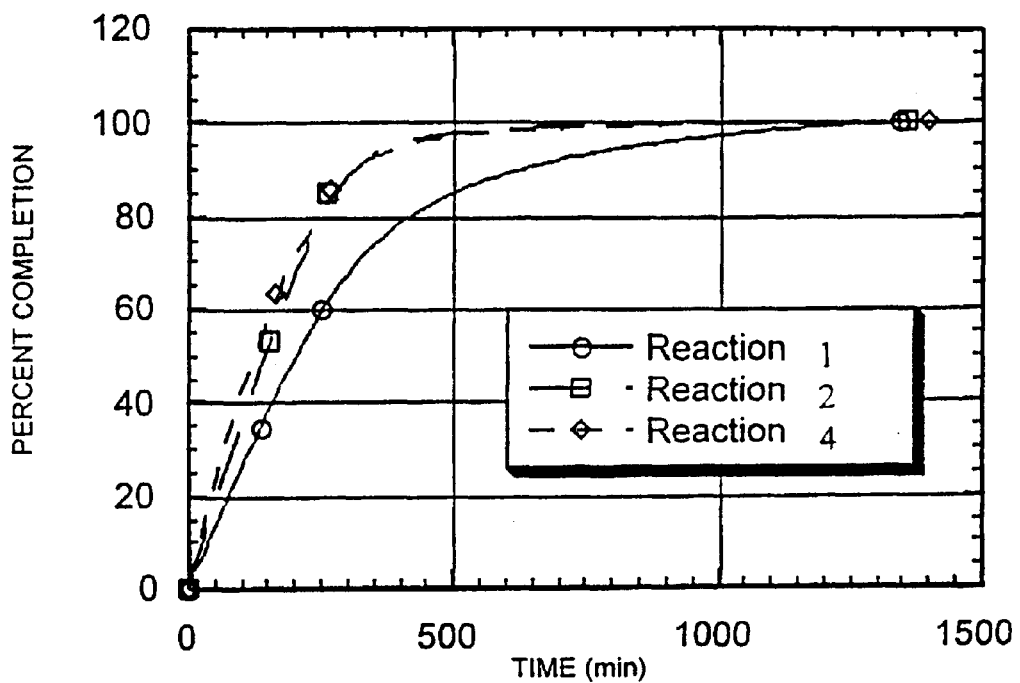
FIG. 1 illustrates graphically the percent completion of the Diels-Alder reactions of compounds 3 (○), 4 (□) and 6 (◇) with N-ethylmaleimide as a function of time. (Example 1).

The present invention includes a novel method for conjugating macromolecules with other molecular entities. Specifically, the present invention describes the use of cycloaddition reactions, in particular the Diels-Alder cycloaddition reaction for the chemoselective and efficient derivatization or conjugation of macromolecules with molecular entities. Thus, a macromolecule bearing either a diene or dienophile moiety is reacted with another molecular entity bearing either a dienophile or a diene moiety, respectively, to yield via Diels-Alder reaction efficient conjugation of the molecular entity to the macromolecule.

The macromolecule can be any large organic molecule which bears or can be derivatized to bear a moiety capable of undergoing a cycloaddition reaction, including but not limited to nucleic acids, oligonucleotides, proteins, peptides, carbohydrates, polysaccharides, glycoproteins, lipids, hormones, drugs or prodrugs. The molecular entity can be any molecule, including another macromolecule, which bears or can be derivatized to bear a moiety capable of undergoing a cycloaddition reaction. Examples of molecular entities include but are not limited to other macromolecules, including antibodies, polymers or resins, such as polyethylene glycol (PEG) or polystyrene diagnostic detector molecules, such as fluorescein, biotin, coumarin or a metal chelator. In a preferred embodiment the cycloaddition reaction is a Diels-Alder reaction and the macromolecule and molecular entity are derivatized with a diene or dienophile, respectively.

Certain terms used to describe the invention herein are defined as follows:

"Nucleoside" as used herein is defined as a modified or naturally occurring deoxyribonucleoside or ribonucleoside or any chemical modifications thereof. Modifications of the nucleosides include, but are not limited to, 2'-, 3'- and 5'-position sugar modifications, 5- and 6-position pyrimidine modifications, 2-, 6- and 8-position purine modifications, modifications at exocyclic amines, substitution of 5-bromo-uracil, and the like. Nucleosides can be suitably protected and derivatized to enable oligonucleotide synthesis by methods known in the field, such as solid phase automated synthesis using nucleoside phosphoramidite monomers, H-phosphonate coupling or phosphate triester coupling.

"Nucleotide" as used herein is defined as a modified or naturally occurring deoxyribonucleotide or ribonucleotide. Nucleotide is a nucleoside as defined above having one or several phosphates or substituted phosphates attached at the 5'-, 2'- or 3'-positions. Nucleotides typically include purines and pyrimidines, which include thymidine, cytidine, guanosine, adenine and uridine.

"Oligonucleotide" refers to a polynucleotide formed from a plurality of linked nucleotide units as defined above. The nucleotide units each include a nucleoside unit linked together via a phosphate linking group. The term oligonucleotide also refers to a plurality of nucleotides that are linked together via linkages other than phosphate linkages such as phosphorothioate linkages. The oligonucleotide may be naturally occurring or non-naturally occurring. In a preferred embodiment the oligonucleotides of this invention have between 1–1,000 nucleotides.

For the purposes of this invention "nucleobase" will have the following definition. A nucleobase is a purine or a pyrimidine base. Nucleobase includes all purines and pyrimidines currently known to those skilled in the art or any chemical modifications thereof. The purines are attached to the ribose ring through the nitrogen in the 9 position of the purine ring and the pyrimidines are attached to the ribose ring through the nitrogen in the 1 position of the pyrimidine ring. The pyrimidine can be modified at the 5- or 6-position of the pyrimidine ring and the purine can be modified at positions 2-, 6- or 8- of the purine ring. Certain modifications are described in copending U.S. patent applications Ser. No. 08/264,029, filed Jun. 22, 1994, entitled "Novel Method of Preparation of Known and Novel 2'-Modified Nucleosides by Intramolecular Nucleophilic Displacement" and Ser. No. 08/458,421, filed Jun. 2, 1994, entitled "Palladium Catalyzed Nucleoside Modifications Methods Using Nucleophiles and Carbon Monoxide" and U.S. Pat. No. 5,428,149, entitled "Method for Palladium Catalyzed Carbon-Carbon Coupling and Products" which are herein incorporated by reference in their entirety. More specifically a nucleobase includes, but is not limited to, uracil, cytosine, N4-protected cytosine, 4-thiouracil, isocytosine, 5-methyluracil (thymine), 5-substituted uracils, adenine, N6-protected adenine, guanine, N2-protected guanine 2,6-diaminopurine, halogenated purines as well as heterocycles meant to mimic the purine or pyrimidine ring, such as imidazole.

"Nucleic acid ligand" as used herein is a nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating a reaction between the target and/or another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In one embodiment, the nucleic acid ligand is a non-naturally occurring nucleic acid. In preferred embodiments of the invention, the nucleic acid ligands are identified by the SELEX methodology. Nucleic acid ligands includes nucleic acids that are identified from a candidate mixture of nucleic acids, said nucleic acid ligand being a ligand of a given target, by the method comprising a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionalitn, to the nucleic acid ligand bases or the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"Non-immunogenic, high molecular weight compound" is a compound of approximately 1000 Da or more that typically does not generate an immunogenic response. An immunogenic response is one that induces the organism to produce antibody proteins. Examples of non-immunogenic, high molecular weight compounds include polyethylene glycol (PEG); polysaccharides, such as dextran; polypeptides, such as albumin; and magnetic structures, such as magnetite.

The term "protein" as used herein refers to a polymer of amino acids, chemically bound by amide linkages (CONH). An "amino acid" is defined as an organic molecule containing both an amino group ($NH_2$) and a carboxylic acid (COOH). Specifically an "amino acid" is any compound of the general formula $R^5CH(NH_2)COOH$ (α-amino acid), wherein $R^5$ is selected from the group consisting of H or any suitably protected known amino acid side chain or any chemical modifications thereof. Suitable protection for amino acid side chains is known to those skilled in the art. As used herein the term "protein" includes peptides, polypeptides and proteins. In a preferred embodiment the proteins of this invention have between 1–500 amino acids.

The term "lipophilic compounds" as used herein refers to compounds which have the propensity to associate with or partition into lipid and/or other materials or phases with low dielectric constants, including structures that are comprised substantially of lipophilic components. Cholesterol, phospholipids, diacyl glycerols and dialkyl glycerols are examples of lipophilic compounds.

A "diene" is defined as a molecule bearing two conjugated double bonds. The diene may even be non-conjugated, if the geometry of the molecule is constrained so as to facilitate a cycloaddition reaction (Cookson (1964) J. Chem. Soc. 5416). The atoms forming these double bonds can be carbon or a heteroatom or any combination thereof.

A "dienophile" is defined as a molecule bearing an alkene group, or a double bond between a carbon and a heteroatom, or a double bond between two heteroatoms.

The dienophile can be any group, including but not limited to, a substituted or unsubstituted alkene, or a substituted or unsubstituted alkyne. Typically, the dienophile is a substituted alkene of the formula C=C—Z or Z'—C=C—Z, wherein Z and Z' are electron withdrawing groups independently selected from CHO, COR, COOH, COCl, COaryl, CN, $NO_2$, aryl, $CH_2OH$, $CH_2Cl$, $CH_2NH_2$, $CH_2CN$, $CH_2COOH$, halogen, or C=C. In certain cases the groups attached to the alkene unit can be electron donating groups, including but not limited to phenyl rings, conjugated double bonds, alkyl groups, OMe groups or other X-alkyl moieties wherein X is an electron donating group (these type of dienophiles under go cycloadditions that are known generally as reverse electron demand cycloadditions). Other examples of dienophiles include compounds having the formula, $R_2C$=X, wherein X is a heteroatom, selected from the group consisting of oxygen, nitrogen, phosphorus and sulfur. For example, molecules bearing a primary amino group, such as amino acids or a lysine containing peptide, can be converted to efficient dienophiles by reaction with formaldehyde to yield their corresponding iminium salts as illustrated in Scheme 1. The latter undergo Diels-Alder cycloaddition with macromolecules bearing a diene group under mild conditions in aqueous solvents.

SCHEME 1

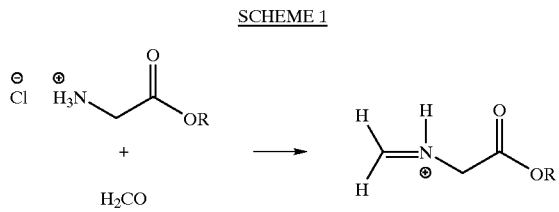

A "1,3-dipole" is defined as a compound that contains a consecutive series of three atoms, a-b-c, where atom a contains a sextet of electrons in its outer shell and atom c contains an octet with at least one unshared pair of electrons in its outer shell. Because molecules which have six electrons in the outer shell of an atom are typically unstable, the a-b-c atom example is actually one canonical structure of a resonance hybrid, where at least one other structure can be drawn. 1,3-dipoles can be divided into two main groups:

1) Systems in which one of the canonical forms has a double bond on the sextet atom (atom a) and the other canonical form has a triple bond on that atom:

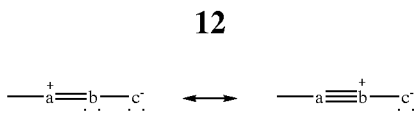

2) Systems where the dipolar canonical form has a single bond on the sextet atom (atom a) and the other canonical form has a double bond on that atom:

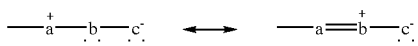

For a review of this reaction type see "Advanced Organic Chemistry" (March, J., ed.) 758–761 (1977) McGraw Hill, N.Y., and "Frontier Orbitals and Organic Chemical Reactions" (I. Fleming) 148–161 (1976) John Wiley and Sons. Ltd. Typical examples include, but are not limited to nitrile ylids, nitrile imines, nitrile oxides, diazoalkanes, azides, azomethine ylids, azomethine imines, nitrones, carbonyl ylids, carbonyl imines and carbonyl oxides.

A "1,3-dipolarophile" is defined in the same manner as a "dienophile" or "diene" (as described above). The macromolecule can be attached to either (or both) the 1,3-dipole or the 1,3-dipolarophile.

A "1,3-dipolar cycloaddition reaction" can be generally represented as follows:

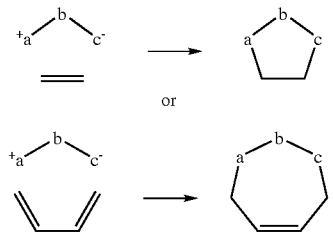

An "Ene reaction" can be generally represented as follows:

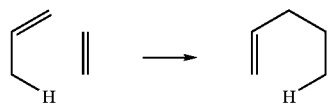

The reaction partners in an Ene reaction are referred to an "ene" and an "enophile." An "enophile" is defined in the same manner as a "dienophile" (see the above description for dienophile). An "ene" can be any unsaturated group, including but not limited to, a substituted or unsubstituted alkene, or a substituted or unsubstituted alkyne. Typically, the "ene" is a substituted alkene of the formula X—C=CH—$CH_2$— or X'—C=CX—$CH_x$—, wherein X and X' are electron donating groups. The macromolecule can be attached to either (or both) the ene component or the enophile component.

As used herein a "macromolecule" refers to a large organic molecule. Examples of macromolecules include, but are not limited to nucleic acids, oligonucleotides, proteins, peptides, carbohydrates, polysaccharides, glycoproteins, lipids, hormones, drugs, or prodrugs.

"Bioconjugate" as defined herein refers to any macromolecule which has been derivatized with another molecular entity. "Bioconjugation" or "Conjugation" refers to the derivatization of a macromolecule with another molecular entity.

The "molecular entity" can be any molecule and can include a small molecule or another macromolecule.

Examples of molecular entities include but are not limited to other macromolecules, polymers or resins, such as polyethylene glycol (PEG) or polystyrene, non-immunogenic high molecular weight compounds, fluorescent, chemiluminescent radioisotope and bioluminescent marker compounds, antibodies, biotin, diagnostic detector molecules, such as a maleimide derivatized fluorescein, coumarin, a metal chelator or any other modifying group. The terms bioconjugation and conjugation are used interchangeably throughout the Specification.

A "derivatized macromolecule" refers to a macromolecule that has been functionalized with a moiety capable of undergoing a cycloaddition reaction. A macromolecule that bears a moiety capable of undergoing a cycloaddition reaction without functionalization also falls within this definition. Examples of moieties capable of undergoing a cycloaddition reaction are defined below as X. In a preferred embodiment the macromolecule is functionalized with a diene or a dieneophile. In a most preferred embodiment the dienophile is a maleimide and the diene is a hexadiene.

The "derivatized oligonucleotides" of this invention are generally represented by the following formulas:

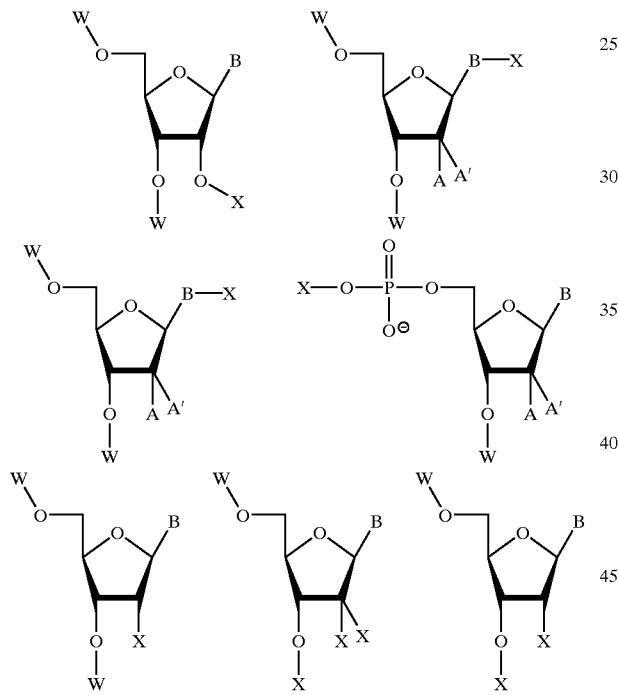

wherein

B is a nucleobase;

A and A' are 2'-sugar substituents;

W is independently selected from the group consisting of an oligonucleotide having between 1–1000 nucleobases, X or H; and X is a diene, dienophile, 1,3-dipole, 1,3-dipolarophile, ene, enophile or other moiety capable of undergoing a cycloaddition reaction additionally, when X is attached to the nucleobase B it can be attached to a carbon atom, an exocyclic nitrogen or an exocyclic oxygen.

In a preferred embodiment of the invention:

A and A' are independently selected from the group consisting of H, $^2$H, $^3$H, Cl, F, OH, NHOR$^1$, NHOR$^3$, NHNHR$^3$, NHR$^3$, =NH, CHCN, CHCl$_2$, SH, SR$^3$, CFH$_2$, CF$_2$H, CR$^2{}_2$Br, —(OCH$_2$CH$_2$)$_n$OCH$_3$, OR$^4$ and imidazole (see U.S. patent application Ser. No. 08/264,029, filed Jun. 22, 1994, entitled "Novel Method of Preparation of 2' Modified Pyrimidines Intramolecular Nucleophilic Displacement," which is incorporated herein by reference);

R$^1$ is selected from the group consisting of H and an alcohol protecting group;

R$^2$ is selected from the group consisting of =O, =S, H, OH, CCl$_3$, CF$_3$, halide, optionally substituted C$_1$–C$_{20}$ alkyl (including cyclic, straight chain, and branched), alkenyl, aryl, C$_1$–C$_{20}$ acyl, benzoyl, OR$^4$ and esters;

R$^3$ is selected from the group consisting of R$^2$, R$^4$, CN, C(O)NH$_2$, C(S)NH$_2$, C(O)CF$_3$, SO$_2$R$^4$, amino acid, peptide and mixtures thereof;

R$^4$ is selected from the group consisting of an optionally substituted hydrocarbon (C$_1$–C$_{20}$ alkyl, C$_2$–C$_{20}$ alkenyl, C$_2$–C$_{20}$ alkynyl), an optionally substituted heterocycle, t-butyldimethylsilyl ether, triisopropylsilyl ether, nucleoside, carbohydrate, fluorescent label and phosphate; most preferably A is selected from the group consisting of H, OH, NH$_2$, Cl, F, NHOR$^3$, OR$^4$, OSiR$^4{}_3$. (See U.S. patent application Ser. No. 08/264,029, filed Jun. 22, 1994, entitled "Novel Method of Preparation of 2' Modified Pyrimidines Intramolecular Nucleophilic Displacement," filed Jun. 22, 1994); and X includes but is not limited to an alkyl or substituted alkyl group bearing a conjugated diene unit, an alkoxy or substituted alkoxy group bearing a conjugated diene unit, CH$_2$=CHCH=CHCH$_2$CH$_2$O—, maleimide substituted alkoxy groups, dienophile substituted alkoxy groups, alkoxy groups, an alkylamino or substituted alkylamino group bearing a conjugated diene unit, maleimide substituted alkylamino groups or substituted alkylamino groups, an alkylamino group or substituted alkylamino group bearing a dienophile moiety, a nitrile ylid, nitrile imine, nitrile oxide, diazoalkane, azide, azomethine ylid, azomethine imine, nitrone, carbonyl ylid, carbonyl imine and carbonyl oxide. The alkyl groups on the above listed substituents can have between 1–50 carbons, preferably 1–30 carbons.

As used herein a "crosslinking molecule" is a molecular entity that connects two or more molecular entities through covalent interactions. More specifically a "crosslinking molecule" is a multifunctional molecule that can be used to derivatize a macromolecule with a diene, dienophile or other moiety capable of undergoing a cycloaddition reaction or a molecule to be conjugated to a macromolecule with a diene, dienophile, or other moiety capable of undergoing a cycloaddition reaction.

The crosslinking molecules of this invention are generally represented by the following formulas:

wherein

X is a diene or dienophile, as defined above;

n is an integer from 1–20; and

L is a linker which includes, but is not limited to, compounds of the following general formula:

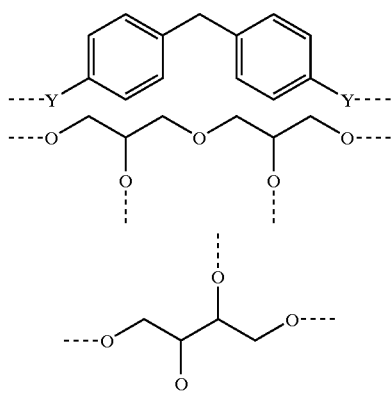

wherein
Y is selected from NH, O, NH(CO)O, NH(CS)O, NH(CO)NH, NH(CO), S—S—S— or Si(R)$_2$ wherein
R is selected from alkyl, aryl, substituted alkyl or substituted aryl.

Other obvious substitutions for the substituents described above are also included within the scope of this invention, which is not limited to the specific, but rather the generalized formula of reaction.

"Therapeutic Agent" means a compound which is used in the treatment of diseases and disorders.

"Diagnostic Agent" means a bioconjugate which can be used for detecting the presence or absence of and/or measuring the amount of target in a sample. Detection of the target molecule is mediated by its binding to a nucleic acid component of a bioconjugate specific for that target molecule. The bioconjugate can be labeled, for example radiolabeled, to allow qualitative or quantitative detection.

"Improved pharmacokinetic properties" means that a bioconjugate shows a longer circulation half-life in vivo relative to a nucleic acid that is not part of a bioconjugate, or has other pharmacokinetic benefits such as improved target to non-target concentration ratio.

Cycloaddition reactions, particularly Diels-Alder reactions, are uniquely suited as a general method for the conjugation of macromolecules to each other, to diagnostic detectors or to other modifying groups. The cycloaddition of a diene to a dienophile is highly chemoselective and only a suitably electronically configured diene and dienophile pair will react. The reaction proceeds under mild conditions in a reasonable time-frame. Macromolecules such as nucleic acids, oligonucleotides, proteins, peptides, carbohydrates, polysaccharides, glycoproteins and lipids generally do not contain moieties that can undergo such a cycloaddition reaction. Thus, by specific introduction of a diene and dienophile reaction partner, macromolecule conjugation, derivatization, or multimerization becomes possible with unprecedented specificity.

The high selectivity of a diene or dienophile for reaction with the corresponding dienophile or diene, respectively eliminates the need to protect functional groups during the synthesis of macromolecules such as oligonucleotides or peptides. This is a tremendous practical advantage over other functional groups used for conjugation in macromolecule synthesis, in which the limited selectivity of the protection chemistry often determines the conjugation yields. Additionally, the diene and dienophiles are not susceptible to the side-reactions typically encountered in conjugation methods. Because, they do not undergo hydrolysis or solvolysis reactions, these reactions can be performed in aqueous media at near stoichiometric concentrations and thus conserve precious reagent. The lack of such side reactions allows dimerization and multimerization of macromolecules in unprecedented yields and purities. The Diels-Alder cycloaddition reaction is accelerated by aqueous solvents and therefore uniquely suited for the derivatization or conjugation of hydrophilic macromolecules. Finally, this conjugation method is much less pH sensitive than most known alternatives.

In one embodiment of the present invention the macromolecule is an oligonucleotide. The solvent of choice for the derivatization of oligonucleotides is water, due to the highly anionic nature of these molecules. Thus, an optimal reaction for the conjugation of such groups to oligonucleotides proceeds readily in water, and displays no side reactions with water, such as hydrolysis of any of the reactants. Based on these criteria for optimal and specific introduction of substituents to oligonucleotides, this disclosure describes the use of Diels-Alder cycloadditions for the chemoselective and efficient modification of oligonucleotides. Thus an oligonucleotide bearing either a diene modified nucleoside or non-nucleoside phosphate diester group, or a dienophile modified nucleoside or non-nucleoside phosphate diester group can be reacted with a molecular entity bearing either a dienophile or a diene moiety, respectively.

The diene or dienophile moiety can be incorporated into the oligonucleotide at any position in the chain, for instance by introduction of a 5-(3,5-hexadiene) 2'-deoxyuridine nucleoside (see U.S. application Ser. No. 08/264,029, filed Jun. 22, 1994, entitled "Novel Method of Preparation of Known and Novel 2'-modified Nucleosides by Intramolecular Nucleophilic Displacement," which is incorporated herein by reference in its entirety). Alternatively, the diene or dienophile moiety can be introduced as the 2'-O-(3,5-hexadiene)uridine nucleoside. A diene moiety can also be introduced to the oligonucleotide as a diene-bearing non-nucleoside phosphoramidite, such as 3,5-hexadiene-N,N-diisopropyl-2-cyanoethyl phosphoramidite. Reaction of the diene modified oligonucleotide, such as a 5'-terminal 3,5-hexadienephosphate oligonucleotide, with the dienophile modified reactant, such as maleimidopolyethylene-glycol methylether, leads to efficient conjugation of the oligonucleotide.

The method of this invention can be extended to the bioconjugation of any macromolecule that can be derivatized with a diene, dienophile or other reactive group capable of undergoing a cycloaddition reaction without limitation. For example, the method can be extended to the conjugation of peptides and proteins with other molecular entities. A peptide or protein that contains an amino acid building block which has been derivatized with a diene or dienophile, such as O-3,5-hexadiene-tyrosine or serine, or N-maleimidolysine, can be conjugated to another molecular entity including, but not limited to, another peptide, an oligonucleotide, nucleic acid, carbohydrate, detector molecule etc. without limitation. Natural macromolecules such as proteins can be derivatized with a diene or dienophile bearing heterobifunctional crosslinking reagent, such as the NHS ester of 3-(4-maleimidophenyl)-propionic acid (Pierce), which allows subsequent conjugation to a macromolecule or diagnostic detector molecule bearing a corresponding diene or dienophile group.

The high chemoselectivity of cycloaddition reactions, particularly the Diels-Alder reaction allows their exploitation for dimerization of macromolecules. When two active macromolecules are combined to a single molecular entity, their activity can be enhanced exponentially. Homobifunctional dimers, comprised of two identical macromolecules, or heterobifunctional dimers, comprised of two molecules with different activity, can be assembled with high specificity and high yield by cycloaddition reaction, particularly by Diels-Alder cycloaddition. For example, an oligonucleotide bearing a diene moiety, such as a 3,5-hexadiene or a cyclopentadiene group, either at the 5'- or 3'-terminus or at a 2'-position or C-5 position anywhere in the sequence can be covalently linked to a second oligonucleotide bearing a dienophile moiety, such as a maleimide or acrylamide group. Such oligonucleotides bearing a diene or dienophile group can react directly with an oligonucleotide bearing a corresponding dienophile or diene group to form dimers. Depending on the point of attachment of the diene or dienophile group, dimers of oligonucleotides can be obtained in either a 5'-3',5'-5', 3'-3',5'-internal, 3'-internal, or internal-internal orientation. Alternatively, such oligonucleotides can react with a crosslinking molecule containing either two or more diene or dienophile groups to form dimers or multimers. Dimerization of oligonucleotides using the method of this invention is illustrated in Examples 2, 4 and 6 below.

Polyethylene glycol is often conjugated to macromolecules to reduce their immunogenicity and to increase their residence time in vivo. The bioconjugation method of this invention allows derivatization of macromolecules, such as oligonucleotides or peptides, bearing a diene, dienophile or other reactive group capable of undergoing a cycloaddition reaction with another polymer or resin, such as polyethylene glycol or polystyrene bearing one or several corresponding diene, dienophile or other groups capable of undergoing cycloaddition reactions.

Macromolecules or molecular entities bearing a dienophile group or other reactive group capable of undergoing a cycloaddition reaction can also undergo cycloadditions to unsaturated lipids bearing diene units or other reactive units capable of undergoing a cycloaddition reaction. The resulting lipid conjugates are useful for anchoring the macromolecules or detector molecules in lipid phases such as micelles or liposomes.

As stated above, conjugation by cycloaddition reactions, particularly the Diels-Alder cycloaddition is not limited to the reaction of macromolecules with each other. It is also extremely useful for the selective derivatization of a macromolecule, such as, an oligonucleotide or peptide, bearing one or several dienes, dienophiles or other reactive groups capable of undergoing a cycloaddition reaction, with a diagnostic detector molecule bearing a diene, dienophile or other group capable of undergoing cycloaddition, such as a maleimide derivatized fluorescein or a maleimide derivatized metal chelator.

The bioconjugation method described herein is also useful to expand the properties and functionality of transcribed oligonucleotides, specifically for the SELEX drug discovery process. The SELEX method is described in U.S. patent application Ser. No. 07/536,428, filed Jun. 11, 1990, entitled "Systematic Evolution of Ligands by EXponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Methods of Identifying Nucleic Acid Ligands," now U.S. Pat. No. 5,270,163 (See also PCT Application Publication No. WO 91/19813). These applications, each specifically incorporated herein by reference, are collectively called the SELEX Patent Applications.

The modification of oligonucleotides by selective conjugation of substituents to multiple modified nucleoside constituents is not limited to oligonucleotides generated by transcription. Nucleoside analogs bearing a reaction center, such as a diene or dienophile, capable of selective reaction with a complementary reactant, such as a dienophile or diene in a cycloaddition reaction, can also be synthetically incorporated into oligonucleotides. A 2'-hexadieneoxyuridine monomer, for example, suitably derivatized to the 5'-protected 3'-phosphoramidite by standard methods, can be incorporated into an oligonucleotide by standard automated solid phase synthesis. This generates a synthetic oligonucleotide bearing multiple internal diene substituents. This oligonucleotide can be conjugated to multiple substituents bearing dienophile groups, such as maleimido polethylene glycol. Thus, a polyethylene glycol coated synthetic oligonucleotide is generated.

Example 1 illustrates the feasibility of using the Diels-Alder reaction for the bioconjugation of macromolecules to other molecular entities. In this example the Diels-Alder reactions of several hexadiene phosphate nucleosides with N-ethylmaleimide is described. The reactions proceed rapidly, in high yields with approximately 1.2 equivalents of maleimide in pure water or 20% iPrOH in water.

Figure 3:
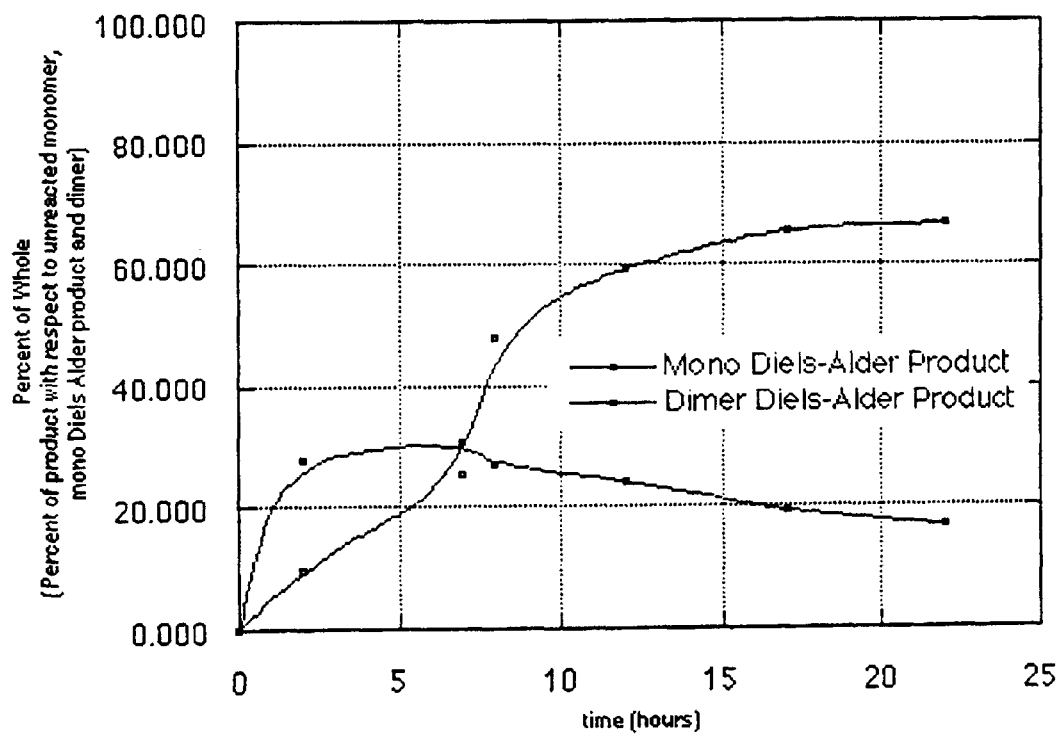
FIG. 3 illustrates graphically the dimerization rate for the Diels-Alder reaction of 5'-DMT-thymidine 3'-hexadiene-(2-cyanoethyl)phosphite with 4,4'-dimaleimidodiphenylmethane. The amount of product was calculated as a percent of unreacted starting material, mono Diels-Alder product (□) and dimer (■).

Example 2 (Scheme 6) describes the dimerization of 5'-DMT-thymidine 3'-hexadiene-(2-cyanoethyl)phosphite (7) with 4,4'-dimaleimidodiphenylmethane dimaleimide (8). FIG. 3 illustrates graphically the amount of mono-Diels-Alder cycloaddition product (mono conjugate) and dimer conjugate present (9) in the reaction mixture over a 22 hour period of time. The amount of the two products was calculated as a percent of unreacted starting material, mono conjugate and dimer conjugate present in the reaction mixture. This graph shows, as expected, that the mono conjugate attains a relatively stable concentration and slowly declines as the dimer conjugate is formed.

Bioconjugation of oligonucleotides depends on the ability to modify the oligonucleotide with a moiety capable of undergoing cycloaddition reaction. One approach is to incorporate the reactive moiety, such as the diene or dienophile into either the sugar or base of a nucleoside, as illustrated in Example 2. A second approach is to prepare a phosphoramidite containing the reactive moiety, which can then undergo coupling and oxidation. The reactive moiety must be able to survive or become unmasked by any deprotection steps. The phosphoramidite may be a 5'-O-terminus for an oligonucleotide chain, or it may have another protected alcohol that may be deprotected for further chain elongation. Examples of compounds which can be used to prepare phosphoramidites containing a diene moiety are set forth in Scheme 2. The synthesis of compounds 11A and 11B is set forth in Example 3 below.

The 3'-O or 5'-O-terminus may also be modified with a charged bis(diene) phosphate via the synthesis of a bis (diene)-ol such as 11D followed by conversion to a phosphoramidite via normal phophoramidite syntheses. This may also be accomplished with the synthesis of a diphosphate ester 11E. It is also possible that a "heterobifunctional" phosphoramidite, exemplified by 11F or 11G, may be a useful compound for crosslinking or a selective two step bioconjugation to different conjugates. Prot represents any standard alcohol protecting group.

SCHEME 2

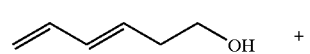

11A

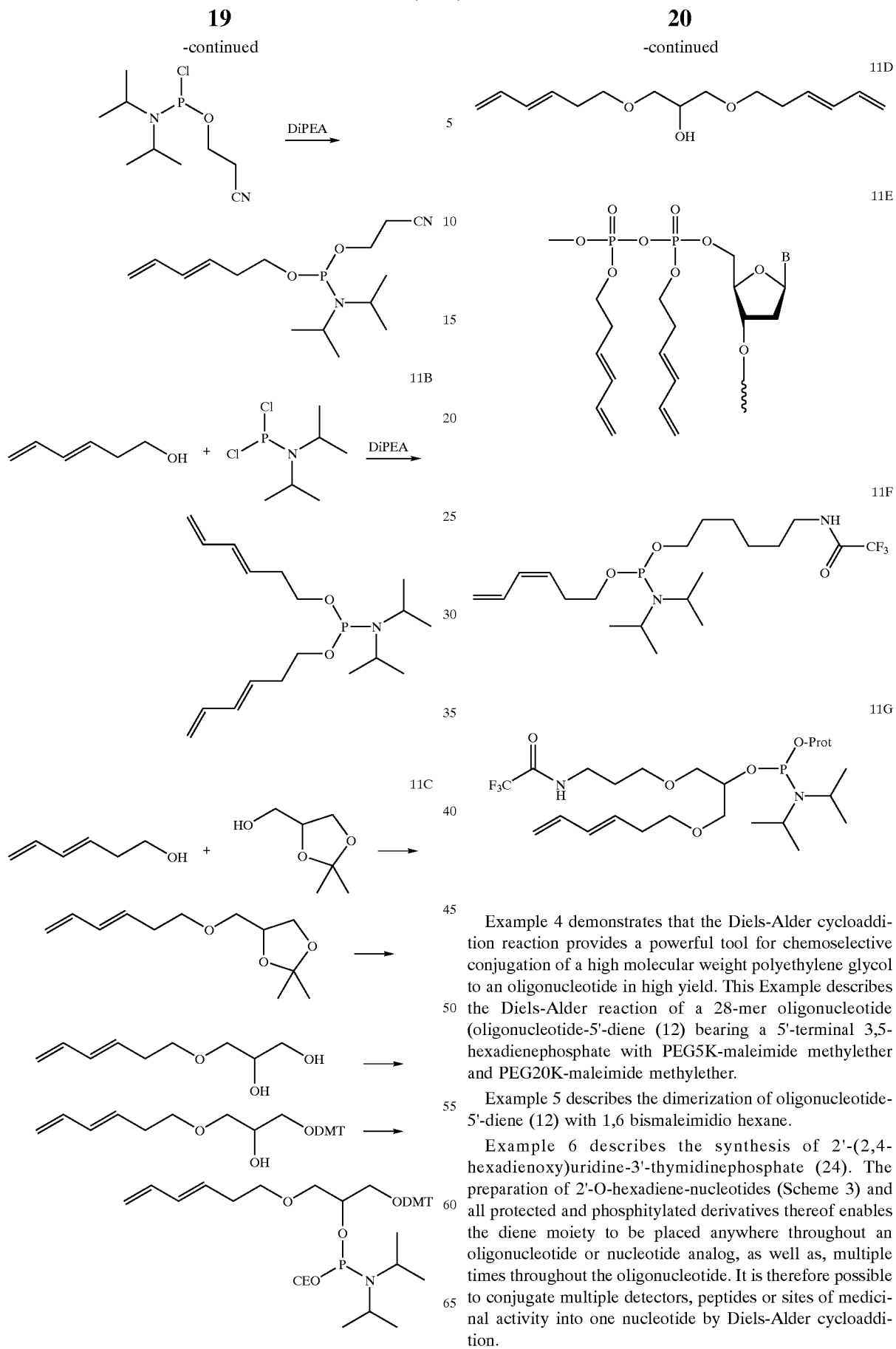

Example 4 demonstrates that the Diels-Alder cycloaddition reaction provides a powerful tool for chemoselective conjugation of a high molecular weight polyethylene glycol to an oligonucleotide in high yield. This Example describes the Diels-Alder reaction of a 28-mer oligonucleotide (oligonucleotide-5'-diene (12)) bearing a 5'-terminal 3,5-hexadienephosphate with PEG5K-maleimide methylether and PEG20K-maleimide methylether.

Example 5 describes the dimerization of oligonucleotide-5'-diene (12) with 1,6 bismaleimidio hexane.

Example 6 describes the synthesis of 2'-(2,4-hexadienoxy)uridine-3'-thymidinephosphate (24). The preparation of 2'-O-hexadiene-nucleotides (Scheme 3) and all protected and phosphitylated derivatives thereof enables the diene moiety to be placed anywhere throughout an oligonucleotide or nucleotide analog, as well as, multiple times throughout the oligonucleotide. It is therefore possible to conjugate multiple detectors, peptides or sites of medicinal activity into one nucleotide by Diels-Alder cycloaddition.

SCHEME 3
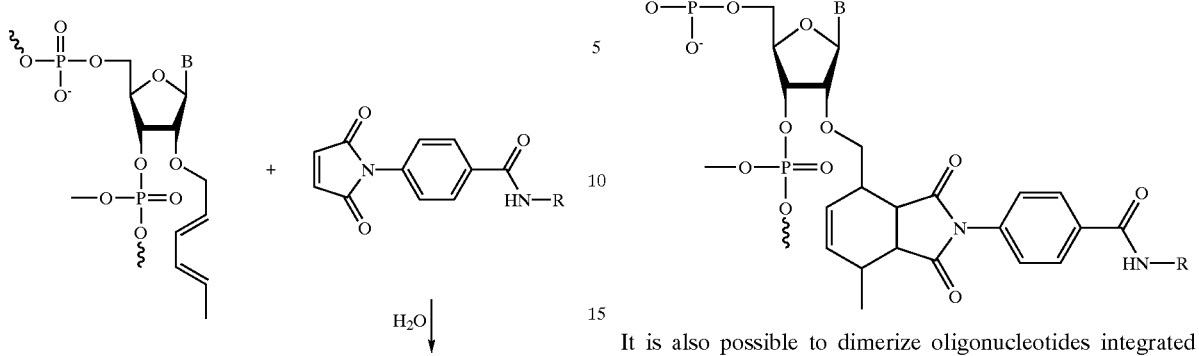
It is also possible to dimerize oligonucleotides integrated with 2'-O-hexadiene-bases as illustrated in Scheme 4. An illustrative dimerization reaction is described in Example 7.
SCHEME 4
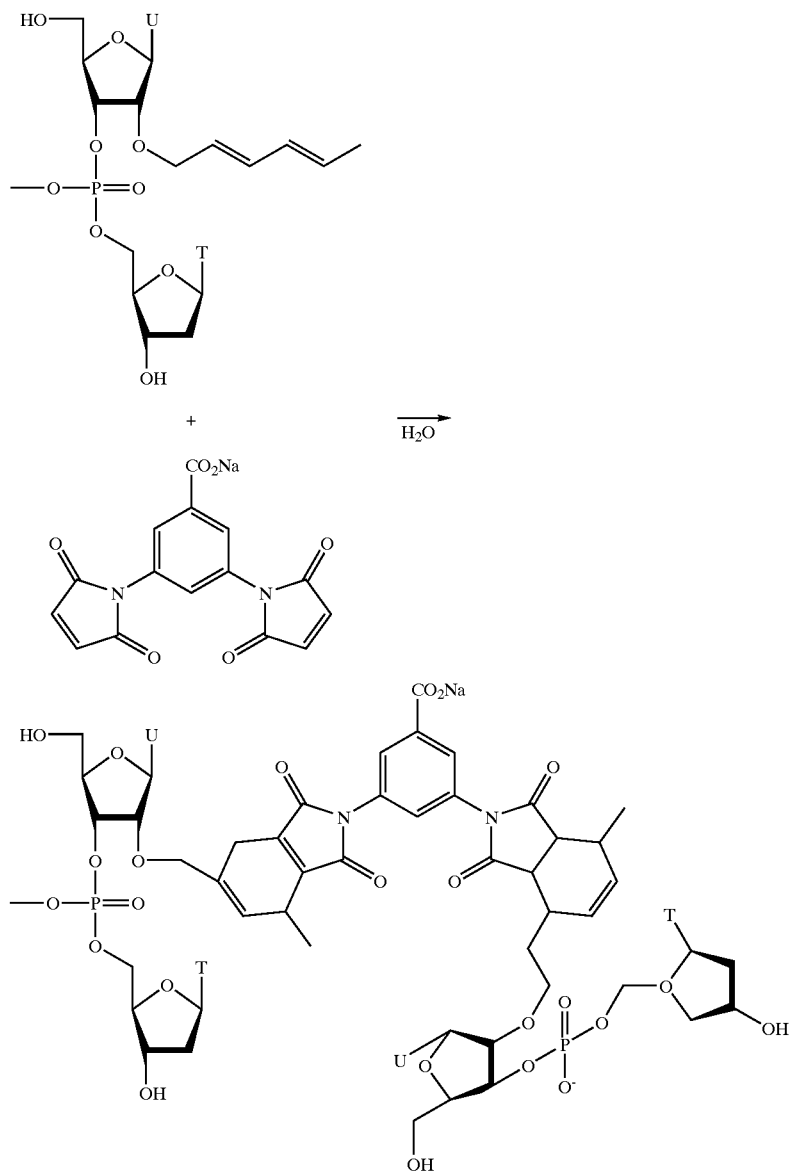

In a study of the Diels-Alder reaction of various substituted maleimides with 2'-(2,4-hexadienoxy)uridine-3'-thymidinephosphate it was found that all water or 20% iPrOH in water soluble maleimides reacted within 30 minutes, while maleimides that were slightly soluble in either of these solvent systems tended to take longer periods of time (>1 hr) and were self-indicating, that is, complete when all solids effected solution.

In a comparison, the rate of cycloaddition reaction of 2'-O-(2,4-hexadiene)uridine-3'-thymidine phosphate (24) (dimer) with sodium 4'-maleimidobenzoate and 2'-O-(2,4-hexadiene)uridine (29) (monomer) with sodium 4'-maleimidobenzoate (Example 8), it was found that the monomer had a $\kappa_{rel}$=6 versus dimer with $\kappa_{rel}$=1. It is postulated that the difference in rate is due to steric factors that may be more pronounced with longer oligonucleotides. Two isomers are detectable via HPLC analysis, both of which are believed to be endo adducts that are differentiated by the 2 possible faces of the diene that may be attacked. These isomers are detected for all Diels-Alder reactions between the dimer and various substituted maleimides that have been performed to date.

Example 9 illustrates the conjugation of oligonucleotide-5'-dienes with various fluorescent detectors. The bioconjugation of the 28-mer oligonucleotide-5'-diene (12) with a maleimide derivatized coumarin proceeded in approximately 90% yield.

Example 10 describes the bioconjugation of a biotin maleimide to an oligonucleotide-5'-diene. This reaction also proceeded in approximately 90% yield.

Example 11 describes the conjugation of a dienophile bearing oligonucleotide to a diene bearing lipid for liposomal anchoring.

Example 12 (Scheme 17) describes the trimerization of oligonucleotide-5'-diene (12). Multimers of oligonucleotides are of interest because increased biological activity is exhibited by anti-sense oligonucleotides that are dimerized, trimerized or linked to a higher degree. Synthesis of multiple maleimido-molecules is possible using either triaminoethyl amine (TREN), dendrimers or other multiple amino compounds.

As stated above cycloaddition bioconjugations are not limited to the Diels-Alder type. They may also be performed using other systems, such as 1,3-dipolar cycloadditions. Although the reactants may have different structures, both types of reactions occur in a concerted fashion, with Diels-Alder cycloadditions giving 6 ember rings and 1,3-dipolar cycloadditions giving 5 member rings. Example 13 illustrates the 1,3-dipolar cycloaddition of 3'-azido-dideoxythymidine (AZT) with N-ethyl maleimide.

Bioconjugation with peptides and proteins is also possible provided that the peptide or protein can be derivatized with a moiety capable of undergoing a cycloaddition reaction. One approach to derivatizing peptides and proteins is to incorporate the reactive moiety into an amino acid, which can then be incorporated into the peptide or protein. Example 14 (Scheme 19) describes the synthesis of the fully protected, diene modified amino acid alcohols (49) and (50). All of the bioconjugations described for oligonucleotides are applicable to peptides and proteins which have been functionalized with a moiety capable of undergoing a cycloaddition reaction. It is possible to incorporate numerous modified amino acids into a peptide for multiple sites of bioconjugation or multimerization. Similarly, other amino acids, such as arginine may be modified for use as a 1,3-dipole for 1,3-dipolar cycloadditions.

The method of this invention can be extended to the preparation of heterodimers. Heterodimerization may be desirable to improve the pharmacokinetics or stability of a macromolecule. As illustrated in Example 15 (Schemes 20–22) a diene functionalized macromolecule, such as an oligonucleotide, peptide or protein, may be conjugated to a dienophile functionalized macromolecule to produce the heterodimer. There may be more than one site of functionalization for either substrate, leading to crosslinking, more than one site of functionalization for only one substrate, giving a branched oligonucleotide, or single site funtionalization for both substrates, giving a heterodimer.

Example 16 (Scheme 24) illustrates the bioconjugation of a macromolecule using an ene cycloaddition reaction. In this example an oligonucleotide is used for purposes of illustration, however the reaction can be performed using any suitably labeled macromolecule. Example 16 also describes the preparation of an oligonucleotide derivatized at the 5'-end with an ene moiety (Scheme 23). As in the case of a diene moiety (discussed above), an ene moiety can be attached to any position on an oligonucleotide.

Example 17 illustrates the bioconjugation of a macromolecule using a [4+3] cycloaddition reaction. In this example an oligonucleotide is used for purposes of illustration, however the reaction can be performed using any suitably labeled macromolecule. Example 17 also describes the synthesis of an oligonucleotide derivatized with a furan.

In one embodiment the method of this invention can be used to synthesize prodrugs. Prodrugs are modified drugs adapted to release the drug after delivery. Often, prodrugs are linked to "carrier" molecules, and ideally, upon reaching their target, they are metabolized to a biologically active compound. Oligonucleotides are ideal carrier molecules in that they are easily conjugated and can be designed to bind to selected targets. Furthermore, large libraries of prodrug conjugated oligonucleotides may be easily synthesized by reacting a diene or dienophile modified nucleoside or nucleotide with a dienophile or diene modified prodrug or small molecule. An example of this is illustrated in Example 18 (Schemes 27 and 28).

The diene or dienophile may be placed anywhere on the sugar or base moiety of a free nucleoside or nucleotide monomer in any covalent manner as illustrated by the following structure:

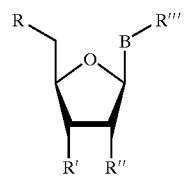

More than one diene or dienophile may be incorporated into a single free nucleoside or nucleotide monomer. Additionally, more than one diene or dienophile modified monomer may be incorporated into an oligonucleotide. The incorporation of numerous prodrug or bioactive molecules could then be bioconjugated to a single nucleoside or nucleotide for more efficient delivery or improved pharmacokinetics.

The transcription of DNA templates catalyzed by a DNA dependent RNA polymerase, such as T7 RNA polymerase, is a prominent method for generation of RNA libraries and for preparation of active RNA molecules such as ribozymes. When such a transcription is initiated with a nucleoside or nucleotide bearing a diene or dienophile group a handle is introduced at the 5'-terminus which allows for subsequent selective conjugation of this RNA transcript to another macromolecule, a diagnostic detector, a crosslinking reagent, or a polymer or resin bearing one or several corresponding diene or dienophile groups. Example 19 describes the conjugation of such a transcript at a specific site on a wafer.

The following examples are presented for illustrative purposes only and are not intended to limit the scope of the invention.

EXAMPLES

Example 1

Diels-Alder Reactions of Hexadiene Phosphate Nucleosides

The concept of addition of a diene phosphoramidite to an oligonucleotide for the purpose of subsequent conjugation to a dienophile bearing moiety was first tested in a model system (Scheme 4). The rate of cycloaddition of the 5'-protected thymidine 3'-(3,5-hexadiene)-(2-cyanoethyl) phosphite triester (3), the corresponding phosphate triester (4), the thymidine 5'-(3,5-hexadiene)-(2-cyanoethyl) phosphite triester (5), and the corresponding phosphate triester (6) with N-ethylmaleimide were compared. In most cases the Diels-Alder reaction was essentially complete within 10 hours at room temperature.

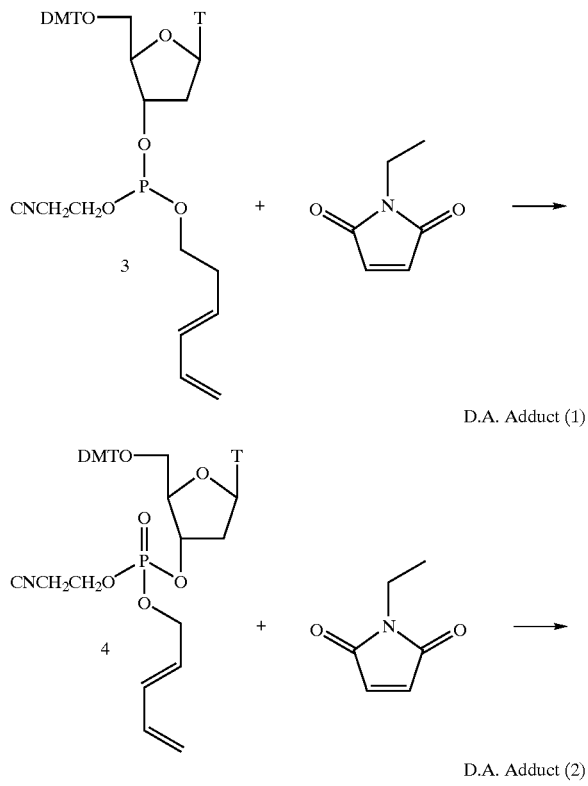

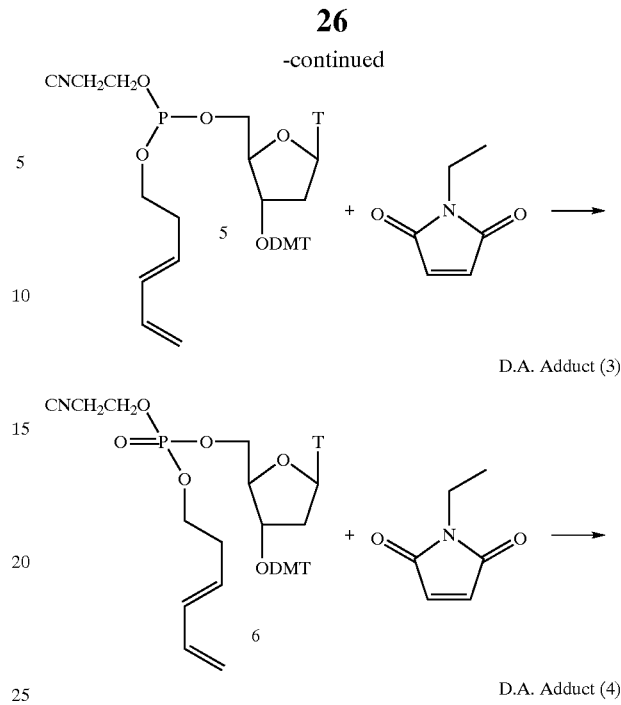

Preparation of the 5'-DMT-thymidine 3'-(3,5-hexadiene)-(2-cyanoethyl)phosphite triester (3)

Compound 3 (Scheme 5) was prepared by reaction of (2-cyanoethyl)-N,N-diisopropyl-3,5-hexadiene phosphoramidite with 5'-O-DMT-thymidine. Briefly, in an argon purged, septum sealed 100 mL round bottom flask, equipped with a stir bar, was placed 5'-O-DMT-thymidine (2.16 g, 4 mmol). The flask was charged with 0.5 M tetrazole in acetonitrile (ACN) (40 mL, 5 equiv.) followed by (2-cyanoethyl)-N,N-diisopropyl-3,5-hexadiene phosphoramidite (4.45 mL, 1.5 equiv.). The reaction was allowed to stir for 45 minutes, during which time the solution turned from cloudy to clear. The mixture was poured into a 250 mL separatory funnel containing ethyl acetate (80 mL). The organic phase was washed twice with 40 mL of 2.5% sodium bicarbonate and once with brine. The organic phase was dried with $MgSO_4$, the solvent was removed and the oil was chromatographed on silica (3:1 ethyl acetate/hexanes, column pre-treated with diisopropyl ethyl amine). The resultant oil was foamed with acetone to yield 2.51 g (85%) of 95+% pure 3 by NMR.

Preparation of the 5'-DMT-thymidine 3'-(3,5-hexadiene)-(2-cyanoethyl)phosphate triester (4)

Into a 100 mL round bottom flask was placed compound 3 (0.37 g, 0.5 mmol) and ACN (20 mL) with stirring. $NaIO_4$ (0.1 M in water, 2.5 equiv.) was added to the stirring mixture and allowed to react for 20 minutes. The mixture was then poured into 100 mL of EtOAc which was washed with water (2×40 mL) and brine (1×40 mL). The organic layer was dried with $MgSO_4$, followed by filtration and solvent removal. The resultant oil was foamed with chloroform to give 0.3 g (80%) of pure 4 by NMR.

Preparation of the thymidine 5'-(3,5-hexadiene)-(2-cyanoethyl)phosphite triester (5)

Compound 5 (Scheme 4) was prepared by reaction of 5'-O-(2-cyanoethyl)-N,N-diisopropyl phosphoramidite thymidine 3'-O-DMT with 3,5-hexadien-1-ol. Briefly, in an argon purged, septum sealed 100 mL round bottom flask, equipped with a stir bar, was placed 5'-O-(2-cyanoethyl)-N,N-diisopropyl phosphoramidite thymidine 3'-O-DMT (0.5 g, 0.68 mmol). The flask was charged with 0.5 M tetrazole in ACN (7 mL. 5 equiv.) followed by 3,5-hexadien-1-ol (0.10 g, 1.5 equiv.). The reaction was allowed to stir for 45 minutes. The mixture was poured into a 250 mL separatory funnel containing ethyl acetate (80 mL). The organic phase was washed twice with 40 mL of 2.5% sodium bicarbonate and once with brine. The organic phase was dried with MgSO$_4$, the solvent was removed and the oil was chromatographed on silica (3:1 ethyl acetate/hexanes, column pretreated with diisopropyl ethyl amine). The resultant oil was foamed with acetone to yield 0.43 g (87%) of 95+% pure 5 by $^1$H and $^{32}$P NMR.

Preparation of the thymidine 5'-(3,5-hexadiene)-(2-cyanoethyl)phosphate triester (6)

Into a 100 mL round bottom flask was placed compound 5 (0.22 g 0.30 mmol) and ACN (10 mL) with stirring. Aqueous 0.1 M NaIO$_4$ (3 mL, 5 equiv.) was added to the stirring mixture and allowed to react for 20 minutes. The mixture was then poured into 50 mL of ethyl acetate which was washed with water (2×40 mL) and brine (1×40 mL). The organic layer was dried with MgSO$_4$, followed by filtration and solvent removal. The resultant oil was foamed with chloroform to give 0.21 g (94%) of pure 6 by NMR.

Measurement of Cycloaddition Reaction Rates

Approximately 0.01 mmol of the diene nucleoside and 1.25 equivalents of N-ethylmaleimide was weighed into an NMR tube. The reaction was dissolved in 0.5 mL of MeCN-d$_3$ and 0.5 mL of deuterium oxide. DMF-d$_7$ was added until all of the precipitate formed dissolved. For NMR measurements, a drop of reaction mixture was removed, placed in another NMR tube, and diluted with an appropriate amount of MeCN-d$_3$, which is used to lock the sample.

Figure 2:
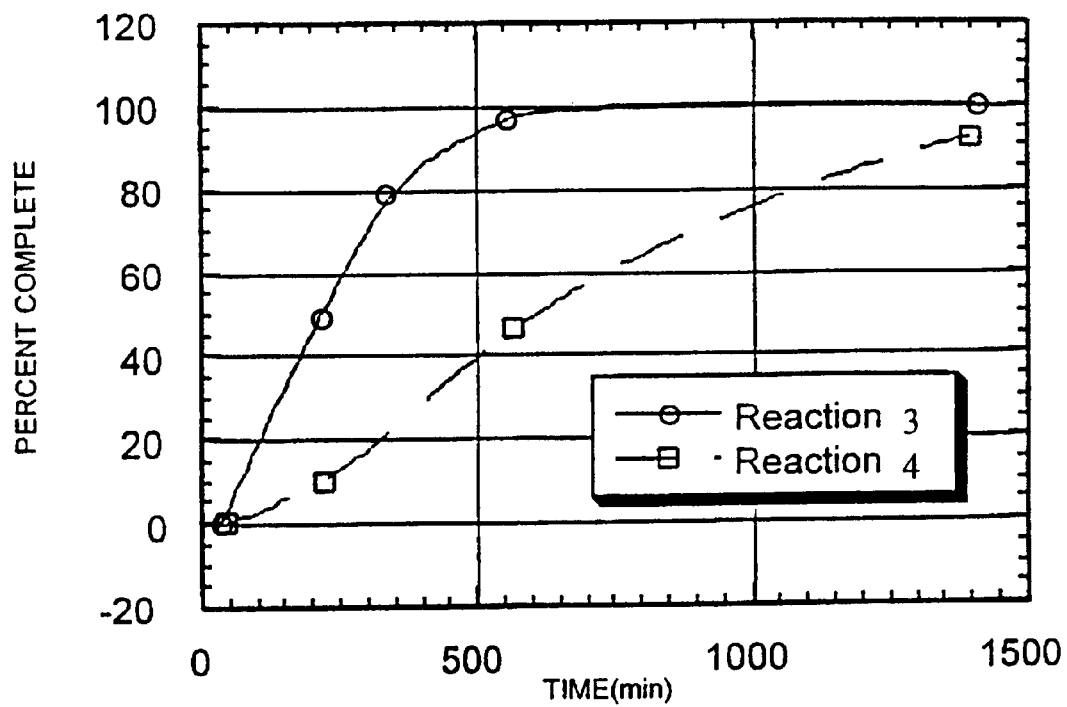
FIG. 2 illustrates graphically the percent completion of the Diels-Alder reactions of compounds 5 (○) and 6 (□) with N-ethylmaleimide as a function of time. (Example 1).

The calculations were made from integration of one aliphatic proton formed during the reaction ($\delta$=5.7) versus the disappearance of a diene proton ($\delta$=6.1). The calculation is the integration of $\delta$=5.7 divided by the sum of both integrations ($\delta$=5.7 and $\delta$=6.1) times 100%. The results of the rate studies are illustrated graphically in FIGS. 1 and 2.

Example 2

Dimerization of 5'-DMT-thymidine 3'-hexadiene-(2-cyanoethyl)phosphite with 4,4'-dimaleimido-diphenylmethane

SCHEME 6

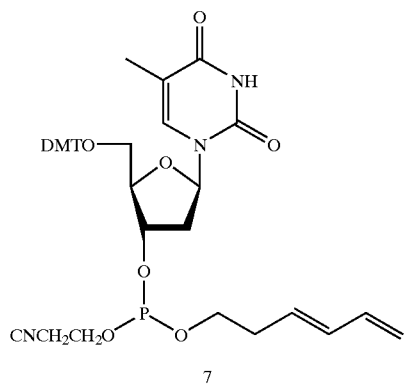

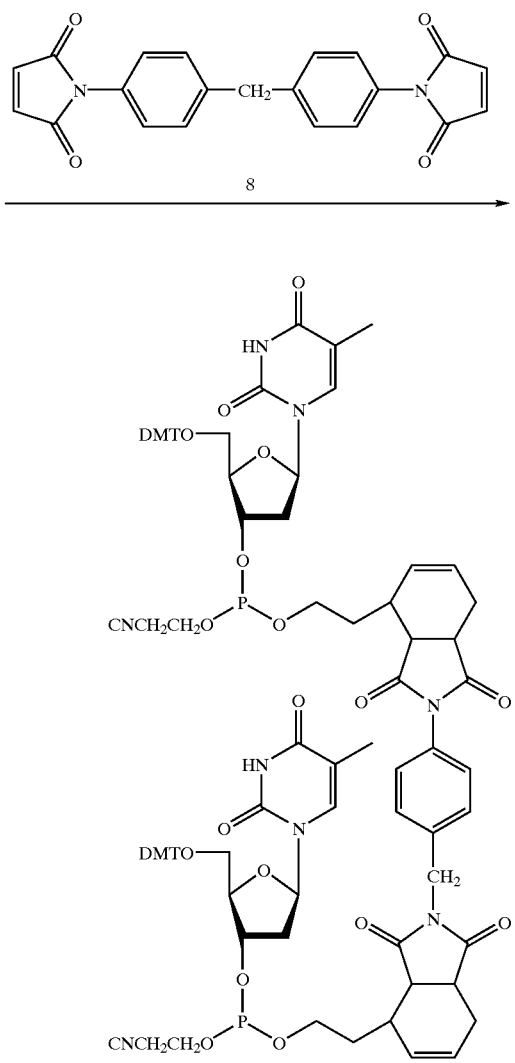

The dimerization of 5'-DMT-thymidine 3'-hexadiene-(2-cyanoethyl)phosphite (7) with 4,4'-dimaleimidodiphenylmethane dimaleimide (8) is illustrated in Scheme 6. The concentration of 5'-DMT-thymidine 3'-hexadiene-(2-cyanoethyl)phosphite was kept at 0.36 M and the concentration of dimaleimide at 1 equivalent. There were few side products. The mixture was sampled intermittently over 22 hours. FIG. 3 illustrates graphically the amount of mono-Diels-Alder cycloaddition product (mono conjugate) and dimer conjugate present (9) in the reaction mixture over the 22 hour period of time.

Example 3

Preparation of Derivatized phosphoramidites

Synthesis of 2-cyanoethyl-(3,5-hexadiene)phosphoramidite (11A).

Into an argon purged, septum sealed round bottom flask was placed 3,5-hexadien-1-ol (2.43 g, 24.8 mmol). The flask was charged with methylene chloride (50 mL) and diisopropylethyl amine (14.5 g, 5.0 equiv.) with stirring. The flask was then charged with 2-cyanoethyl-N,N'-diisopropylchlorophosphoramidite (5.00 g, 22.5 mmol) and stirred for 45 minutes. The reaction mixture was diluted to 100 mL with methylene chloride and then washed with 2.5% $NaHCO_3$ (2×50 mL) and brine (1×50 mL). The organic phase was dried with $MgSO_4$, the solvent removed and the oil dried under high vacuum for 18 hours to yield compound 11A in 99+% purity by $^1H$ NMR and $^{31}P$ NMR.

Synthesis of bis(3,5-hexadiene)-N,N'-diisopropyl phosphoramidite (11B).

Into an argon purged, septum sealed round bottom flask was placed 3,5-hexadien-1-ol (2.56 g, 26.1 mmol). The flask was charged with methylene chloride (50 mL) and diisopropylethyl amine (16.0 mL, 5.0 equiv.) with stirring. The flask was was then charged with N,N'-diisopropyl phosphoramidous dichloride (2.5 g, 12.4 mmol) and allowed to stir for 45 minutes. The reaction mixture was diluted to 100 mL with methylene chloride then washed with 2.5% $NaHCO_3$ (2×50 mL) and brine (1×50 mL). The organic phase was dried with $MgSO_4$, the solvent removed and the oil dried under high vacuum for 18 hours to yield compound 11B in 99+% purity by $^1H$ NMR and $^{31}P$ NMR.

Example 4

Conjugation of PEG-maleimide methylether to a 28-mer oligonucleotide bearing a 5'-terminal 3,5-hexadienephosphate

SCHEME 7

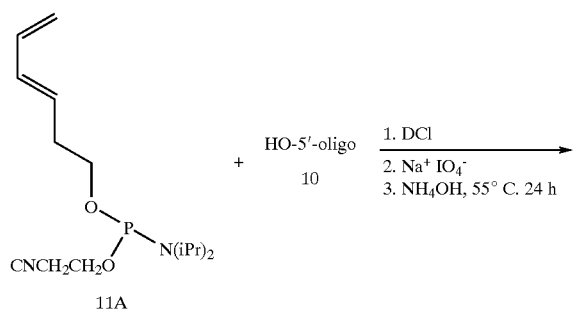

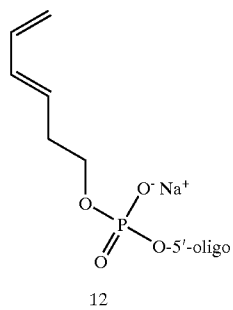

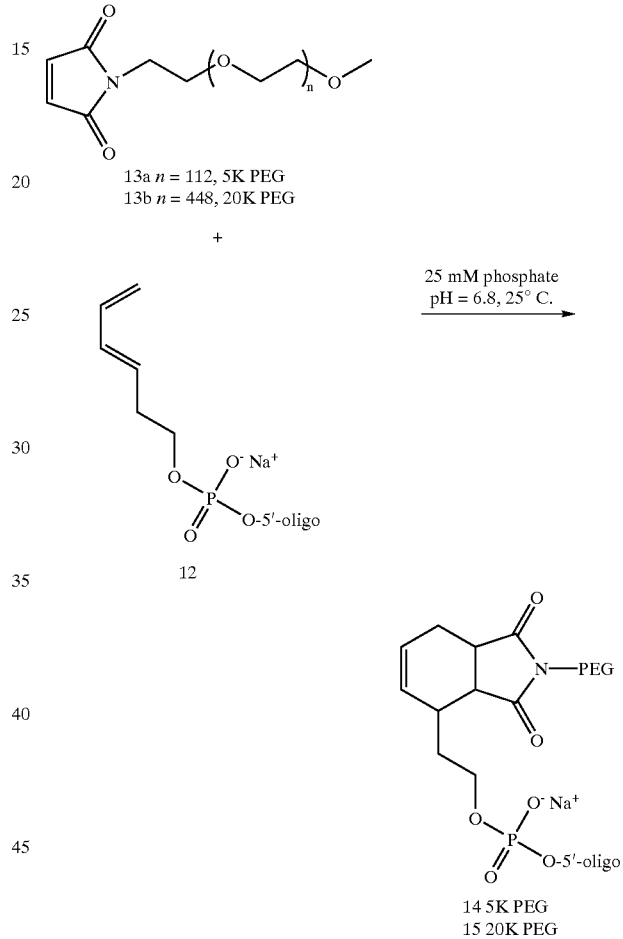

Oligonucleotide Synthesis

A 28-mer DNA having the sequence 5'-HO-CCAGTACAAGGTGCTAAACGTAATGG[3'3'T]T-3' (10) was prepared on a Milligen 8800 oligonucleotide synthesizer using standard solid phase protocols at the 300 μmole scale. After completion of the 5' terminal solid phase addition cycle, the 3,5 hexadiene-1-ol phosphoramidite (11A) was added (0.2M acetonitrile solution, 4 equivalents dicyanoimidazole (DCI). 30 minutes coupling time) to form the corresponding phosphite triester (Scheme 7). The phosphite triester was then oxidized with 0.5M $NaIO_4$ in water for 10 minutes to form the desired phosphate triester. The excess oxidant was removed by washing with water followed by acetonitrile. Use of the standard iodine oxidation protocol resulted in destruction of the diene moiety. The oligonucleotide was cleaved from the solid support and deprotected under standard conditions. Anion exchange analysis of the crude deprotected oligonucleotide showed 45% full length oligonucleotide-5'-diene.

The crude oligonucleotide-5'-diene was purified by reverse phase HPLC on a Hamilton PRP-1 column using a tetrabutylammoniun bromide/acetonitrile gradient. The purified oligonucleotide was pooled and the tetrabutylammonium salt exchanged for sodium on the PRP-1 column, the excess sodium was removed with a water wash and the sodium salt of the oligonucleotide was eluted with approximately 50% acetonitrile. The purified oligonucleotide (12) was then lyophilized to a white powder. This material was 90% pure by anion exchange HPLC (Dionex Nucleopak strong anion exchange column, Tris/sodium chloride gradient at 85° C.). This material was analyzed by mass spectroscopy (electrospray), expected mass=8796; observed mass=8796.

5K Polyethylene Glycol Conjugation

Figure 4:
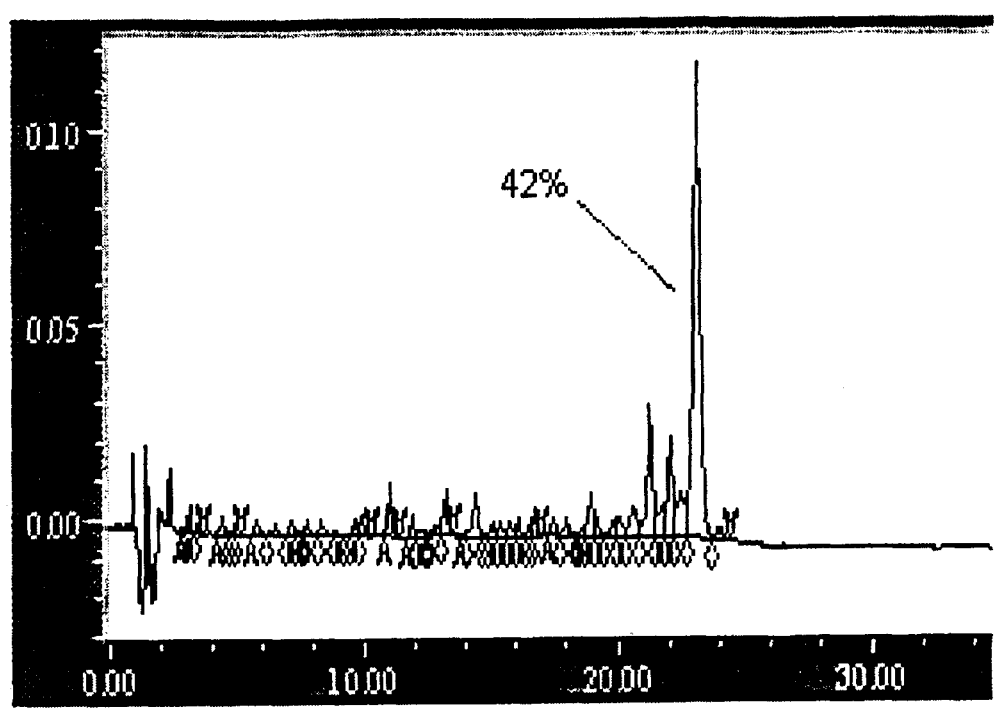
FIG. 4 illustrates the reverse phase HPLC of the crude 5'-hexadienoxy-phosphate-DNA (12). The peak at 23 minutes (42% by area integration) corresponds to the full-length oligonucleotide product 12.
Figure 5:
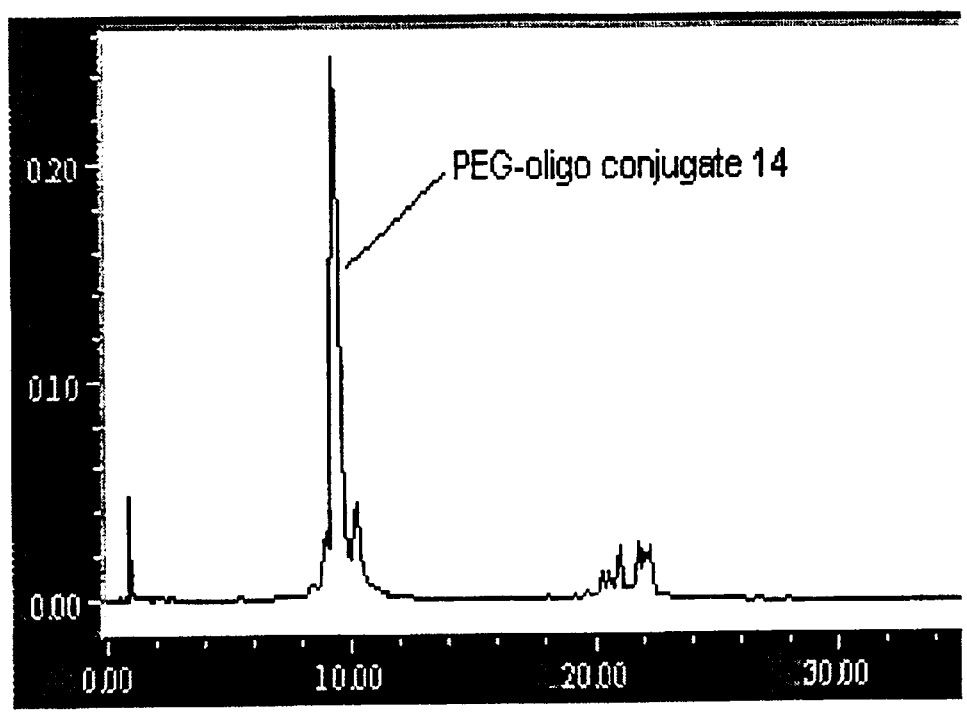
FIG. 5 illustrates the reverse phase HPLC of the crude polyethylene glycol-DNA conjugate (14). The peak at 9.5 minutes (80% by area integration) corresponds to the PEG-oligo conjugate product 14.

The lyophilized oligonucleotide-5'-diene (12) was dissolved in 25 mM phosphate (pH=6.8, 8 μM, approximately 74 mg/mL). To this solution was added two equivalents of monomethoxy-PEG-maleimide (13a) (MW=5,000, Shearwater Polymers) (Scheme 7). After 18 hours at 25° C. all of the diene labeled oligonucleotide had undergone coupling with the maleimide-PEG to give the 5K PEG Diels-Alder product (14). The product was isolated by reverse phase chromatography. (See FIGS. 4 and 5).

A similarly prepared oligonucleotide sample that lacked the 5' diene label did not couple to the maleimide PEG. Addition of acetonitrile to the Diels-Alder reaction slowed down the conjugation rates. The addition of 10% acetonitrile slowed the rate by nearly half the value in water alone. These oligo-5'-dienes thus behave like small non charged dienes in their reactivity in aqueous solution.

20K Polyethylene Glycol Conjugation

The lyophilized oligonucleotide-5'diene (12) was dissolved in 25 mM phosphate (pH=6.8, 5 μM, approximately 55 mg/mL). To this solution was added two equivalents of monomethoxy-PEG-maleimide (13b) (MW=20,000, Shearwater Polymers) (Scheme 7). After 18 hours at 25° C. all of the diene labeled oligonucleotide had undergone coupling with the maleimide-PEG to give the 20K PEG Diels-Alder product (15). The product was isolated by reverse phase chromatography.

Example 5

Conjugation of oligonucleotide-5'-diene (12) with 1,6 bismaleimidio hexane

SCHEME 8

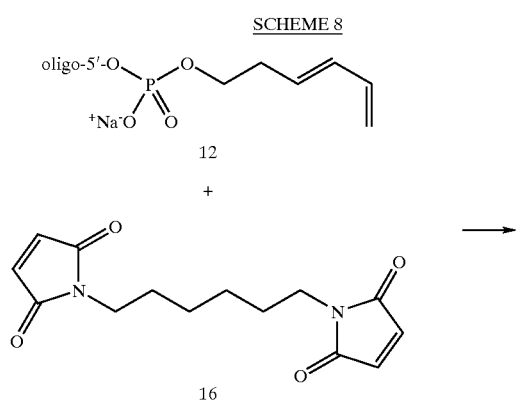

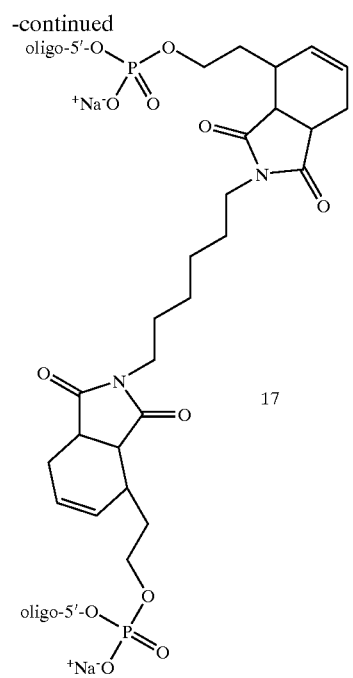

A solution of oligonucleotide (12) was treated with 1/3 an equivalent of 1,6-bismaleimidio hexane (16) (Pierce) at 25° C. (Scheme 8). After 16 hours the dimer conjugate (17), had formed in approximately 80% yield (based on maleimide), very little mono conjugate was obtained. The dimer product was isolated by anion exchange chromatography and analyzed by mass spectroscopy (electrospray), expected mass=17872 observed mass=17873.

Diels-Alder adducts have also been prepared with N-ethyl maleimide. Briefly, approximately two equivalents of N-ethyl maleimide was added to an aqueous solution of oligonucleotide-5'-diene (12) at 25° C. After four hours the reaction was complete. The products were isolated by anion exchange chromatography and analyzed by mass spectroscopy (electrospray), expected mass=8921 observed mass=8922.

Example 6

Preparation of a 2'-O-(2,4-hexadiene)uridine-3'-O-thymidinephosphate

DMT-anhydrouridine is known to undergo reaction with Mg(R)$_2$ (where R=alkoxy) to yield 2'-substituted nucleosides. As demonstrated below, this chemistry can be used to prepare nucleosides substituted at the 2'-position with a diene. The 2'-substituted nucleoside can then be incorporated into a nucleotide or nucleotide analog. This is demonstrated by the solution phase synthesis of 2'-O-(2,4-hexadiene)uridine-3'-O-(5'-O-acetylthymidine)phosphate (24) (Scheme 9).

SCHEME 9

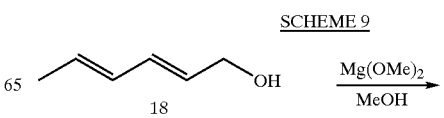

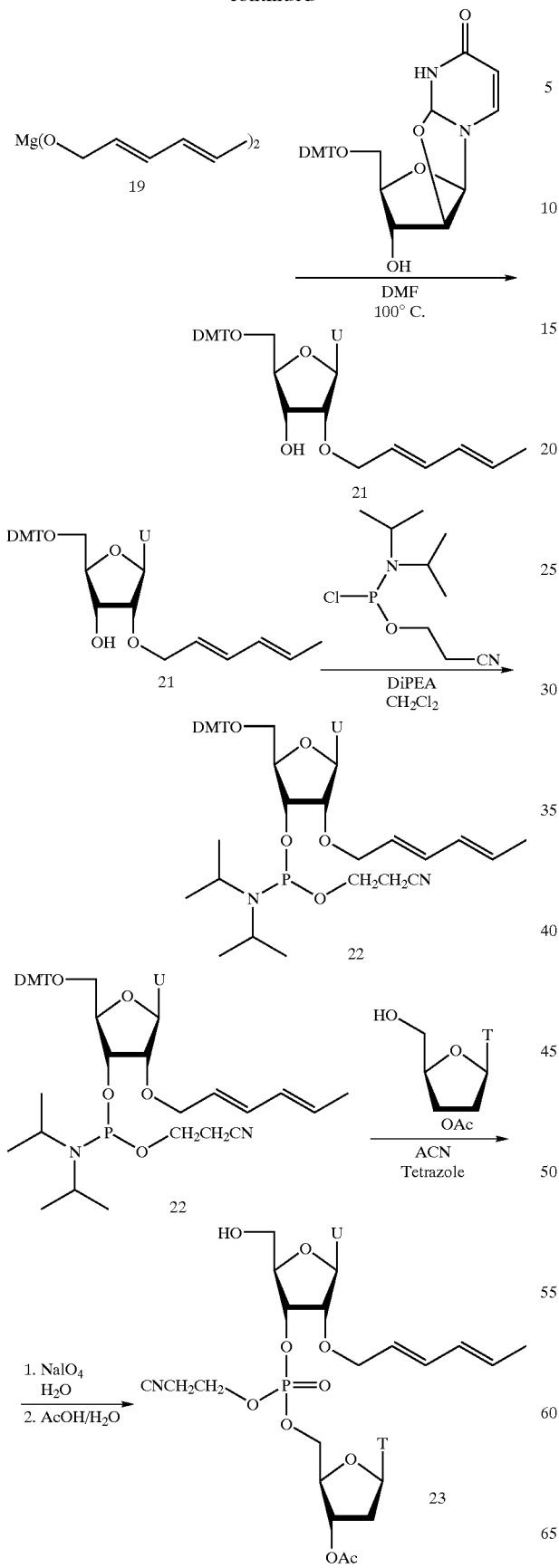

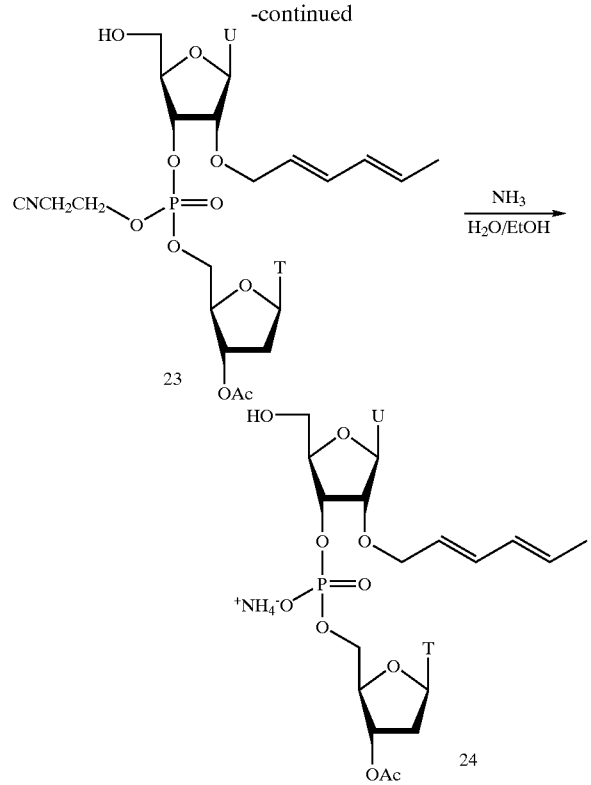

Preparation of 5'-O-DMT-anhydrouridine (20)

Into a 1 L round bottom flask was weighed anhydrouridine (22.67 g, 100 mmol). 4,4'-dimethoxytrityl chloride (33.34 g, 1.1 equiv.) and DMAP (1.0 g, catalytic). A stir bar was added, the flask was septum sealed and flushed with argon. The flask was then charged with pyridine (300 mL) and the mixture stirred for 72 hours. The pyridine was removed in vacuo and the residual oil was redissolved in EtOAc (200 mL) for washing with 2.5% $NaHCO_3$ (2×100 mL) and brine (1×100 mL). The organic phase was dried with $MgSO_4$, filtered and the solvent was removed resulting in a yellow oil. The oil was purified with a silica column (1:1 EtOAc/hexane, 1% diisopropylethylamine) resulting in 5'-O-DMT-anhydrouridine (20) (24.21 g, 45.7%) that had no impurities by $^1$H NMR.

Preparation of 5'-O-DMT-2'-O-(2,4-hexadiene) uridine (21)

Into a 250 mL round bottom flask was placed 2,4-hexadien-1-ol (18) (37.31 g, 380.1 mmol) and the flask was sealed and argon purged. The flask was then charged with 1.1 mmol/mL methanolic $Mg(OMe)_2$ (75 mL, 82.5 mmol) and stirred for 1 hour. The methanol was removed in vacuo, followed by coevaporation with toluene, giving a red oil (19). 5'-O-DMT-anhydro-uridine (20) (11.30 g, 21.34 mmol) was added to the flask followed by an argon purge and warming to 100° C. The flask was then charged with DMF (80 mL) and allowed to stir for 4 hours. The reaction mixture was poured into ethyl acetate (500 mL) and washed with aqueous 5% ammonium chloride (2×100 mL), saturated aqueous sodium bicarbonate (1×100 mL) and brine (1×100 mL). The aqueous phases were back extracted with ethyl acetate (3×100 mL). The organic phase was combined, dried with $MgSO_4$, filtered and the solvent was removed in vacuo.

The orange/brown oil was chromatographed on silica with a 0%, 20%, 50%, 70% gradient of ethyl acetate in hexanes to give 10.05 g of product (21) (75%) that was pure by $^1$H NMR.

Preparation of 5'-O-DMT-2'-O-(2,4-hexadiene) uridine-3'-O-cyanoethyl-N,N'-diisopropyl phosphoramidite (22)

5'-O-DMT-2'-O-(2,4-hexadiene)uridine (21) (3.00 g, 4.80 mmol) was placed in a 250 mL round bottom flask that was septum scaled and argon purged. The flask was charged with methylene chloride (25 mL). DiPEA (5.85 mL, 7 equiv.) and cyanoethyl-N,N'-diisopropylchlorophosphoramidite (2.14 mL, 2 equiv.). The reaction mixture was stirred for 45 minutes. The mixture was then washed with aqueous 2.5% NaHCO$_3$ (2×50 mL) and brine (1×50 mL), dried with MgSO$_4$, filtered and the solvent was removed in vacuo. The yellow oil was chromatographed with silica and 1:1 EtOAc/hexanes to afford 3.14 g (80%) of 5'-O-DMT-2'-O-(2,4-hexadiene)uridine-3'-O-cyanoethyl-N,N'-diisopropylphosphoramidite (22) that was pure by $^1$H NMR.

Preparation of 2'-O-(2,4-hexadiene)uridine-3'-O-(5'-O-acetylthymidine)cyanoethyl phosphate (23)

5'-O-DMT-2'-O-(2,4-hexadiene)uridine-3'-O-cyanoethyl-N,N'-diisopropyl phosphoramidite (22) (2.18 g, 2.64 mmol) and 3'-O-acetylthymidine (0.7523 g, 2.65 mmol) were placed in a 250 mL round bottom flask equipped with a stir bar. The flask was charged with 0.5 M tetrazole in ACN (25 mL, 4.5 equiv.) with stirring. The reaction was stirred for 25 minutes then washed with aqueous 2.5% NaHCO$_3$ (2×50 mL) and brine (1×50 mL). The resulting wet oil was taken up in ACN (30 mL) and treated with aqueous 0.5 M NaIO$_4$ (13 mL, 2.5 equiv.). The mixture was stirred for 10 minutes, then poured into EtOAc (100 mL) before washing with water (2×50 mL) and brine (1×50 mL). The organic phase was dried with MgSO$_4$, filtered and the solvent was removed to afford a white solid. The solid was dissolved in AcOH/H$_2$O (4:1) and stirred for 1 hour. The acid and water was removed in vacuo. The oil was dissolved in MeCl$_2$ and precipitated with ether. The solid was then filtered and collected. The precipitation was performed 2 additional times on the supernatent. The solid was purified on silica (7% MeOH in MeCl$_2$) to afford 1.56 g (81.9%) of 2'-O-(2,4-hexadiene)uridine-3'-O-(5'-O-acetylthymidine) cyanoethylphosphate (23) that was pure by $^1$H NMR.

Preparation of 2'-O-(2,4-hexadiene)uridine-3'-O-(5'-O-acetylthymidine)phosphate (24)

2'-O-(2,4-hexadiene)uridine-3'-O-(5'-O-acetylthymidine) cyanoethylphosphate (23) (1.36 g, 1.89 mmol) was dissolved with gentle heating in EtOH (40 mL). The solution was transferred to a 250 mL Pyrex® screw cap bottle with a Teflon® lined cap. Concentrated ammonium hydroxide (150 mL) was added, the cap replaced and the bottle was vigorously shook and the initial pressure relieved. The bottle was then placed in a incubated shaker at 37° C. after re-tightening the cap. The mixture was allowed to shake for 4.5 hours. The solvent was removed in vacuo, the foam was redissolved in H$_2$O/MeOH (1:1) and precipitated by ACN at −20° C. overnight, yielding 1.08 g of white crystalline 2'-O-(2,4-hexadiene)uridine-3'-O-(5'-O-acetylthymidine) phosphate (24) that was pure by $^1$H NMR with no acetamide contamination.

Example 7

Dimerization of 2'-O-(2,4-hexadiene)uridine-3'-thymidine phosphate with sodium 3,5-bismaleimidobenzoate

SCHEME 10

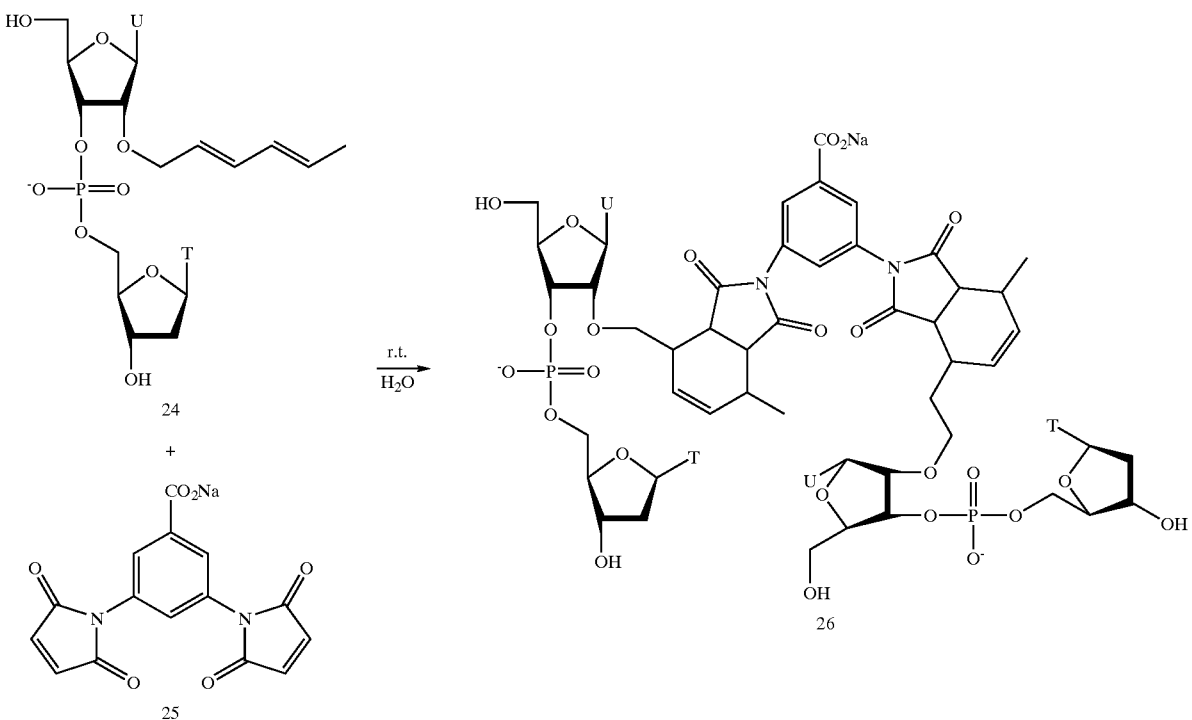

2'-O-(2,4-hexadiene)uridine-3'-thymidine phosphate (24) (20.1 mg, 0.031 mmol) was placed into a screw cap vial with sodium (3,5-bismaleimidobenzoate (25) (4.9 mg, 0.5 equiv.) and the mixture was dissolved in 1 mL of D$_2$O (Scheme 10). $^1$H NMR and HPLC analysis (run as described in Example 8) show complete conversion to dimerized 2'-O-(2,4-hexadiene)uridine-3'-thymidine phosphate (26).

Example 8

Diels-Alder Reactions of 2'-O-(2,4-hexadiene)uridine-3'-thymidine phosphate and sodium 4-maleimidobenzoate

SCHEME 11

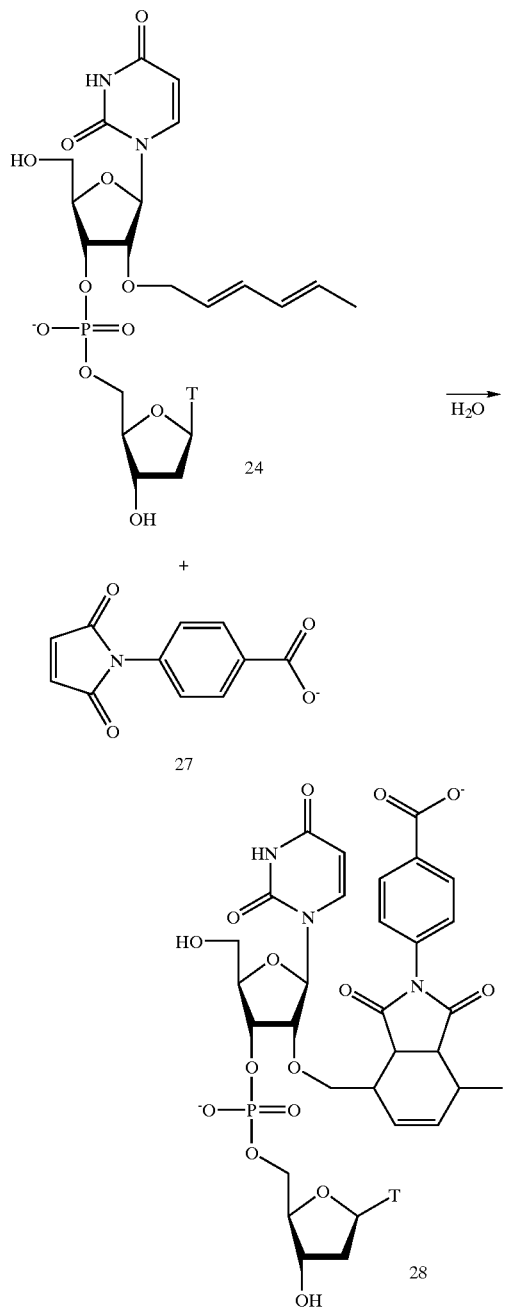

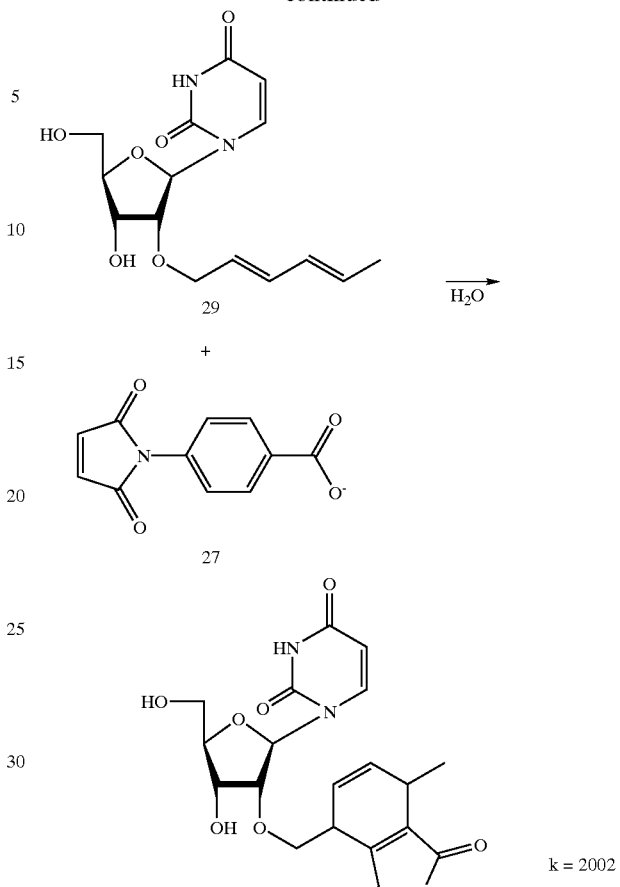

2'-O-(2,4-hexadiene)uridine-3'-thymidine phosphate (24) (21.5 mg, 0.0334 mmol) was weighed into a screw cap vial with sodium 4-maleimidobenzoate (27) (82.5 mg, 10 equiv.) and dissolved in 1 mL of D$_2$O. 200 μL was sampled periodically over 30 minutes and diluted to 600 μL with acetonitrile-d$_3$. The reaction was kept at 0° C. until analysis via HPLC or $^1$H NMR. HPLC analysis was performed on a BioCad 60 instrument fitted with an analytical Waters Delta-Pak C-18 column using a 0–15% acetonitrile gradient in 100 mM triethylamine/acetic acid buffer (pH=7) run over 6 column volumes.

The reaction 2'-O-(2,4-hexadiene)uridine (29) (monomer) with sodium 4-maleimidobenzoate (27) was performed using the same reaction conditions to yield the Diels-Alder cycloaddition product (30).

Example 9

Conjugation of a Fluorescent Detector to a 2'-hexadiene Bearing Dimer Oligonucleotide Example 9 (Schemes 12–15) illustrates the conjugation of oligonucleotide-5'-dienes with various fluorescent detectors.

Preparation of 4'-maleimidophenylbutyramide conjugated fluorescein (33)

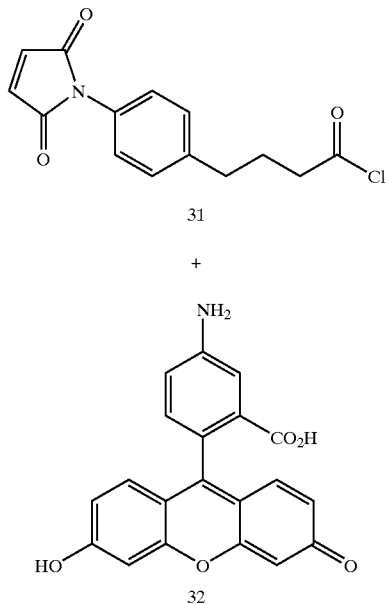

Diels-Alder reaction of oligonucleotide-5'-diene (12) with Compound (33)

SCHEME 13

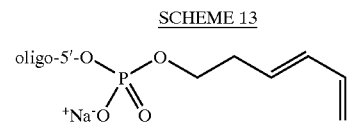

12

+

Fluorescein is commonly used as a fluorescent label for biologically interesting compounds. Fluorescamine (32) (Scheme 12), a commercially available amine derivatized fluorescein (a deep burgundy solid), was attached to maleimidophenyl-butanoic acid. Amidolysis was achieved via the acid chloride of the maleimide-acid (31). The reaction was smooth followed by a relatively easy separation via column chromatography to yield a bright orange solid (33).

Approximately two equivalents of compound (33) were added to an aqueous solution of the oligonucleotide-5'-diene (12) at 25° C. After 20 hours the reaction was complete. The product (34) was isolated by reverse phase chromatography.

Diels-Alder Reaction of 2'-O-(2,4-hexadiene)
uridine-3'-O-(5'-O-acetylthymidine)phosphate (24)
with Compound (33)
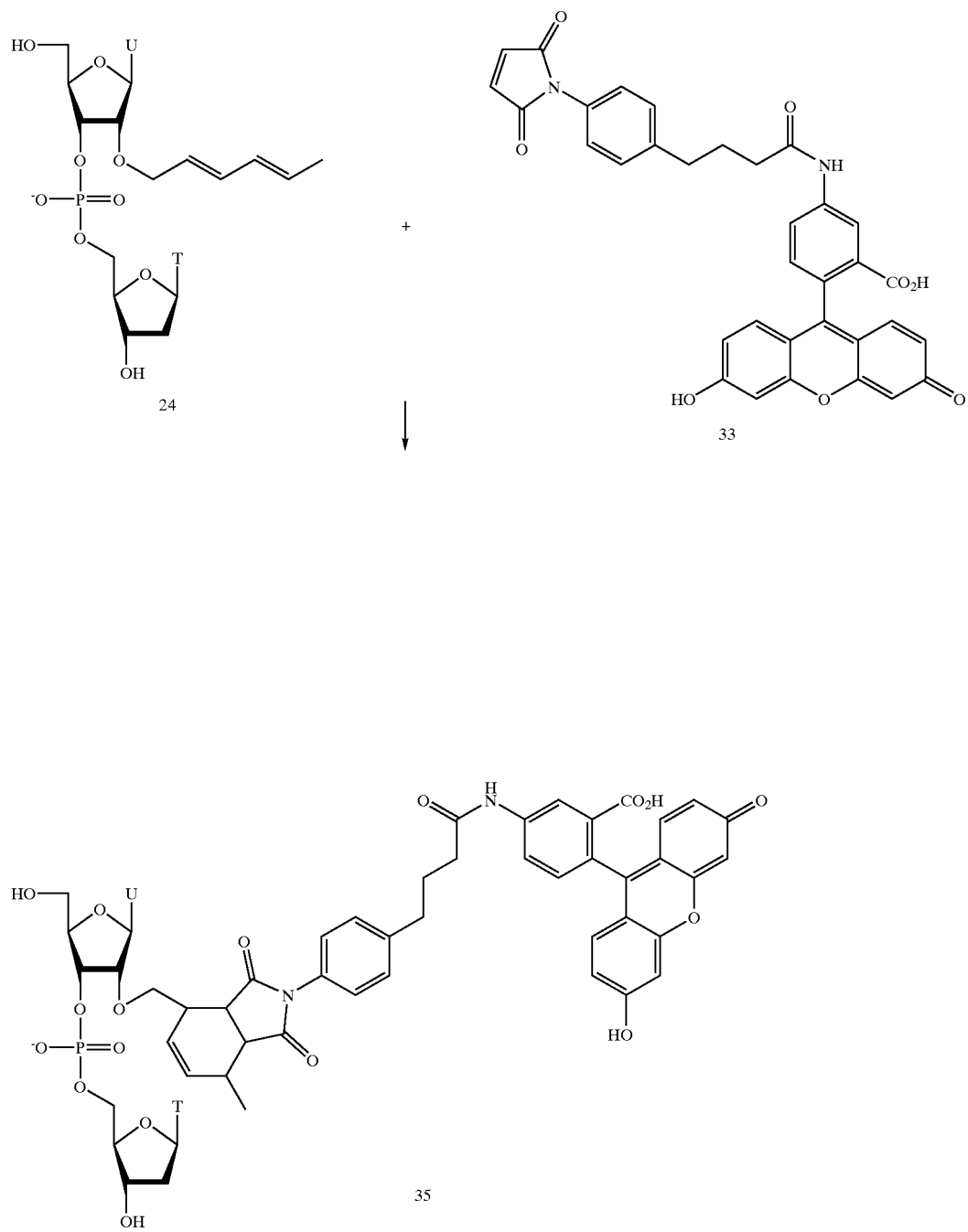
SCHEME 14

Compound (24) (10.2 mg, 15.9 μmol) was weighed into a screw top vial and dissolved in 800 μL of H$_2$O. 4'-Maleimidophenylbutyramide conjugated fluorescein (33) (37.3 mg, 63.4 μmol) was dissolved in 800 μL of iPrOH. 200 μL of fluorescein-conjugate solution was then added to the 2'-hexadiene bearing dimer oligonucleotide solution to yield Diels-Alder conjugate (35). The reaction mixture was monitored by HPLC analysis of 100 μL samples of the reaction mixture diluted to 500 μL with 1:1 H$_2$O:iPrOH.

Diels-Alder Reaction of oligonucleotide-5'-diene (12) with coumarin maleimide Derivative (36)

SCHEME 15

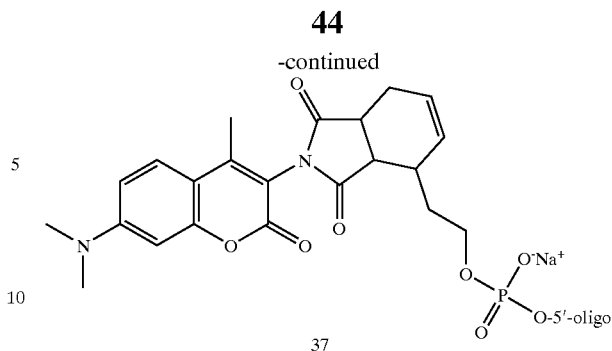

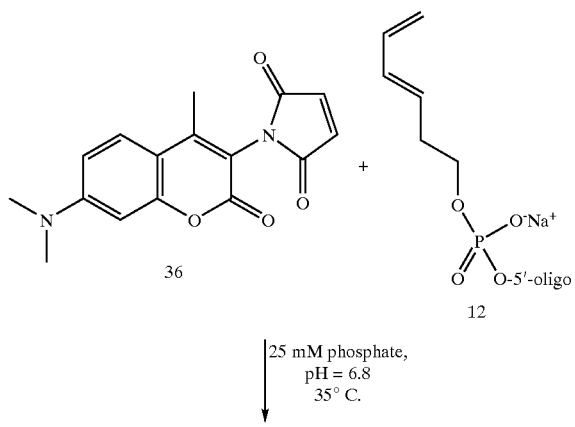

Approximately 1.3 equivalents of compound (36) a coumarin maleimide derivative (Aldrich Chemical) was added to an aqueous solution of the oligonucleotide-5'-diene (12) at 35° C. After 60 hours the reaction was complete. The product (37) was isolated by anion exchange chromatography (in approximately 90% yield) and analyzed by mass spectroscopy (electrospray), expected mass=9096 observed mass=9097.

Example 10

Conjugation of a biotin maleimide to oligonucleotide-5'-diene (12)

SCHEME 16

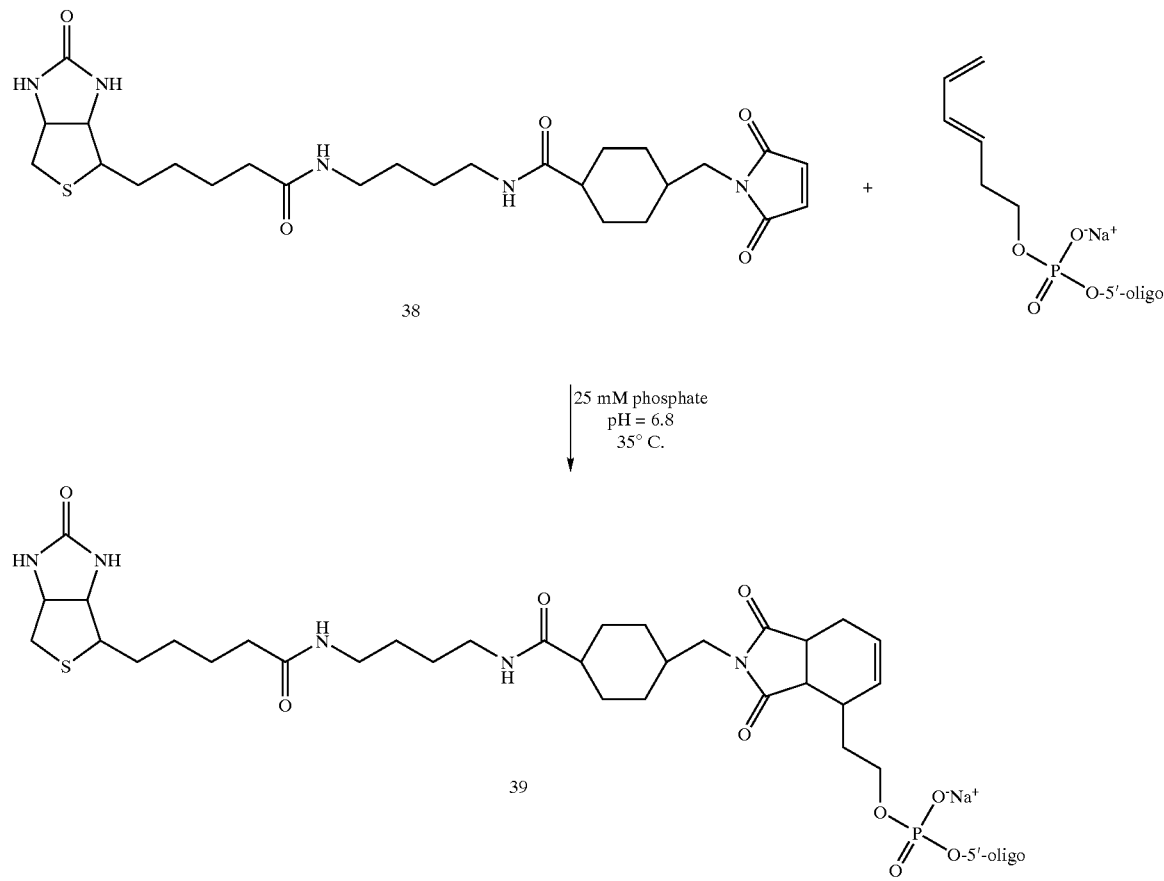

Approximately 2 equivalents of biotin maleimide (38) were added to an aqueous solution of the oligonucleotide-5'-diene (12) at 35° C. After 18 hours the reaction was complete. The product (39) was isolated by an anion exchange chromatography (in approximately 90% yield) and analyzed by mass spectroscopy (electrospray), expected mass=9332 observed mass=9333.

Example 11
Conjugation of a Dienophile Bearing oligonucleotide to a Diene Bearing Lipid for Liposomal Anchoring A phospholipid bearing a diene unit can be used to anchor an oligonucleotide in the lipid bilayer of a liposome. A lipid such as linoleic acid is isomerized to the corresponding conjugated diene derivative under acidic conditions. This derivative is subsequently converted to the corresponding phospholipid. The phospholipid is poised to react with dienophiles in an aqueous environment to form adducts by cycloaddition. Due to the nature of the phospholipid orientation in a liposome, the adduct is located in the lipid bilayer (see U.S. application Ser. No. 08/434,465, filed May 4, 1995, entitled "Nucleic Acid Ligand Complexes" which is incorporated herein by reference in its entirety). Treatment of a maleimide derivatized oligonucleotide with a diene containing phospholipid would lead to the formation of a lipid oligonucleotide conjugate as formed by the Diels-Alder reaction.

Example 12
Multimerization of oligonucleotides

SCHEME 17

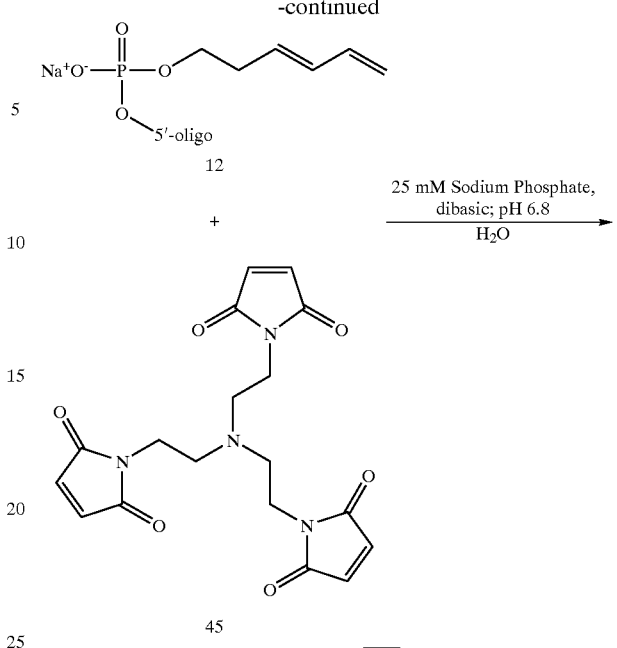

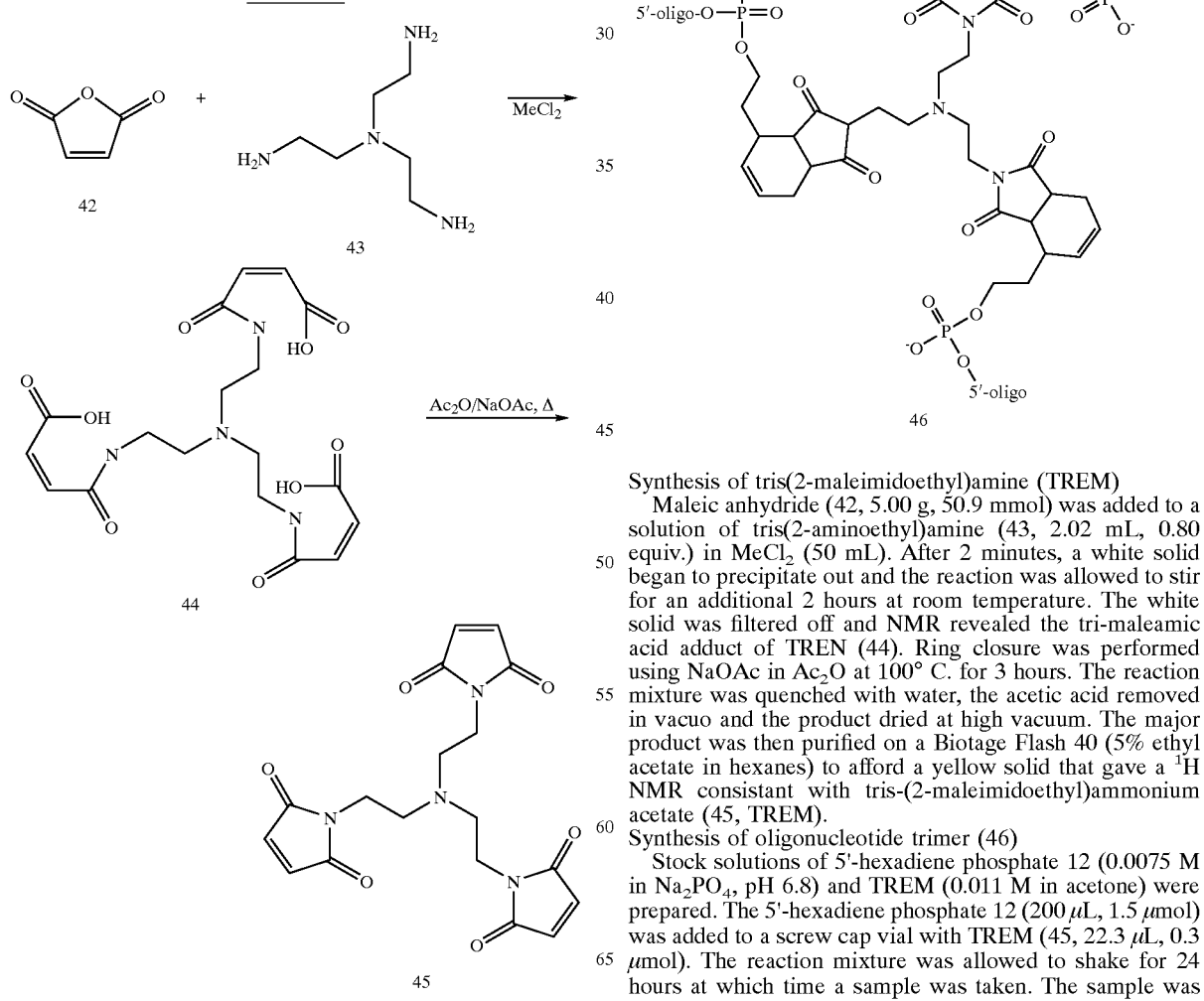

Synthesis of tris(2-maleimidoethyl)amine (TREM)

Maleic anhydride (42, 5.00 g, 50.9 mmol) was added to a solution of tris(2-aminoethyl)amine (43, 2.02 mL, 0.80 equiv.) in MeCl$_2$ (50 mL). After 2 minutes, a white solid began to precipitate out and the reaction was allowed to stir for an additional 2 hours at room temperature. The white solid was filtered off and NMR revealed the tri-maleamic acid adduct of TREN (44). Ring closure was performed using NaOAc in Ac$_2$O at 100° C. for 3 hours. The reaction mixture was quenched with water, the acetic acid removed in vacuo and the product dried at high vacuum. The major product was then purified on a Biotage Flash 40 (5% ethyl acetate in hexanes) to afford a yellow solid that gave a $^1$H NMR consistant with tris-(2-maleimidoethyl)ammonium acetate (45, TREM).

Synthesis of oligonucleotide trimer (46)

Stock solutions of 5'-hexadiene phosphate 12 (0.0075 M in Na$_2$PO$_4$, pH 6.8) and TREM (0.011 M in acetone) were prepared. The 5'-hexadiene phosphate 12 (200 µL, 1.5 µmol) was added to a screw cap vial with TREM (45, 22.3 µL, 0.3 µmol). The reaction mixture was allowed to shake for 24 hours at which time a sample was taken. The sample was analyzed by HPLC (Dionex DNA column, 3.1 mL volume;

36–78% Buffer B over 16 column volumes; Buffer A: 25 mM Trizma, 1 mM EDTA, 10% ACN in H₂O; Buffer B: Same as Buffer A plus 1 M NaCl). The fractions of trimer (46) were collected and characterized via mass spectroscopy with an expected mass of 26777 and a measured mass of 26793, well within expected error of ±3%.

Example 13

Bioconjugation via 1,3-cycloaddition

SCHEME 18

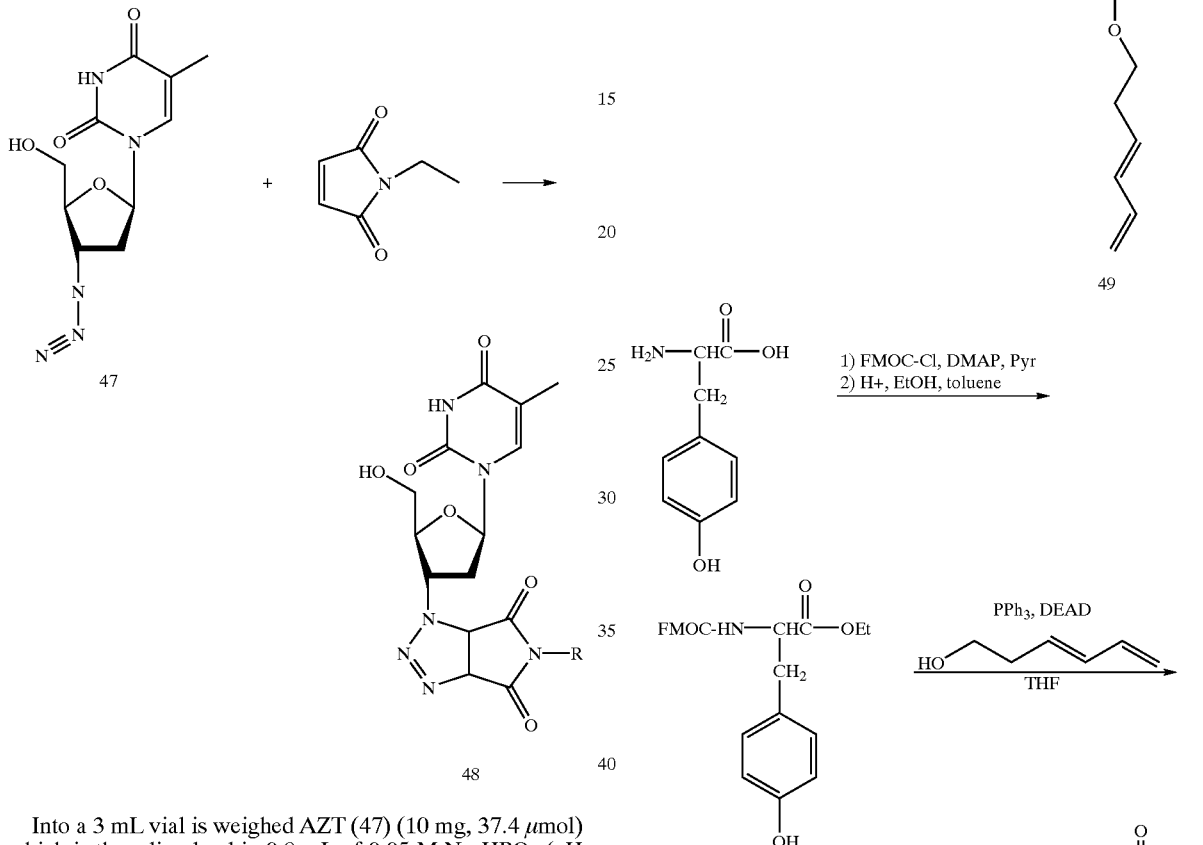

Into a 3 mL vial is weighed AZT (47) (10 mg, 37.4 μmol) which is then dissolved in 0.8 mL of 0.05 M Na₃HPO₄ (pH 12). N-Ethyl maleimide ((9.4 mg, 75 μmol) is weighed into a separate vial and dissolved in 1 mL of ethanol. Into the vial containing the AZT is placed 0.2 mL of the N-ethyl maleimide solution. The vial is capped, shaken well for 5 minutes and then allowed to react at 45° C. for 3 hours to yield compound (48). A 100 μL aliquot of the reaction mixture is diluted to 700 μL, mixed well and analyzed via HPLC (Jupiter C-18 column, 2–40% acetonitrile in 100 mM triethylamine/acetic acid pH 7 buffer over 7 column volumes).

Example 14

Preparation of Diene Modified Amino Acids

Scheme 19 illustrates the synthesis of the fully protected, diene modified amino acids (49) and (50).

SCHEME 19

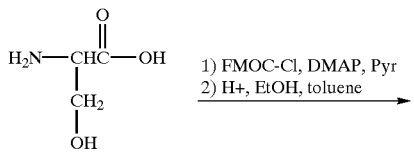

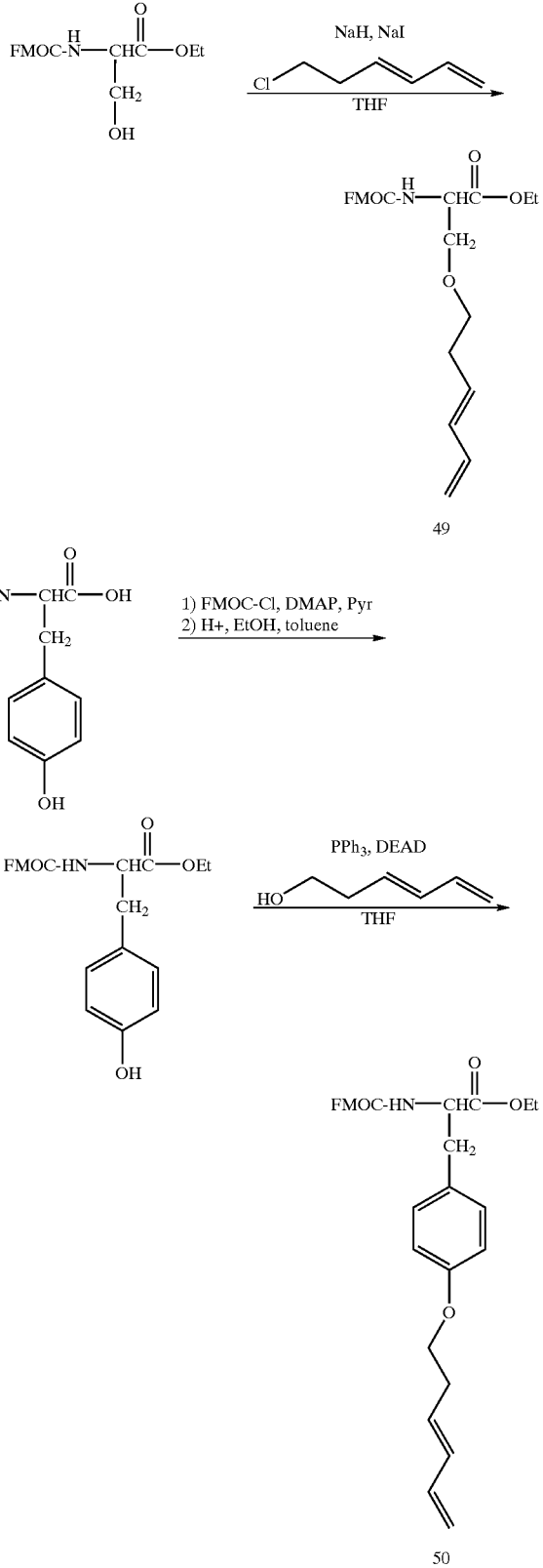

Example 15

Formation of "Heterodimers" of oligonucleotides

Scheme 20 illustrates the heterodimerization of two macromolecules each of which has more than one site of functionalization leading to a crosslinked product.

SCHEME 20
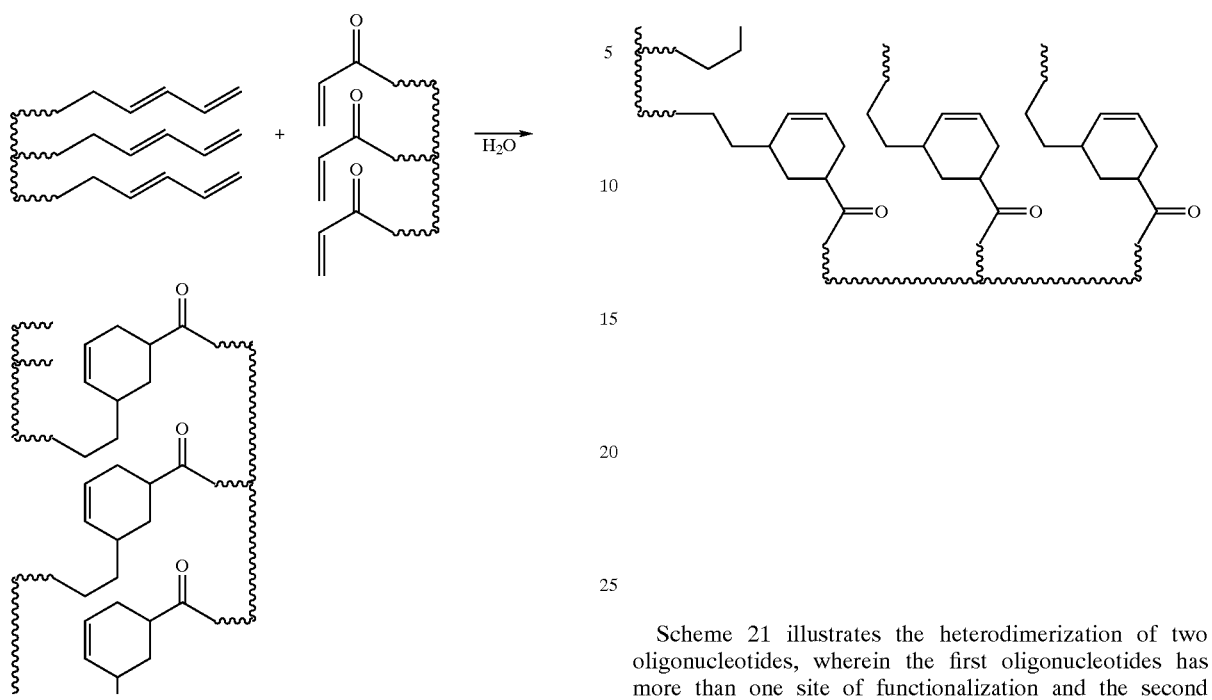
Scheme 21 illustrates the heterodimerization of two oligonucleotides, wherein the first oligonucleotides has more than one site of functionalization and the second oligonucleotide has only a single site of functionalization giving a branched oligonucleotide product.
SCHEME 21
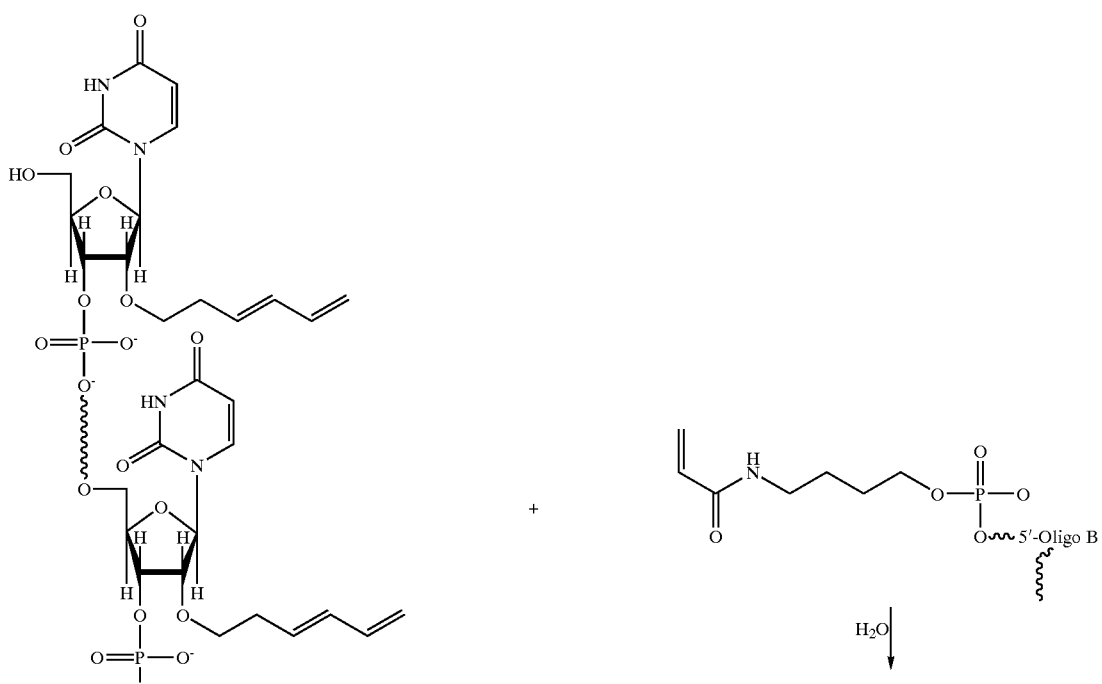

-continued
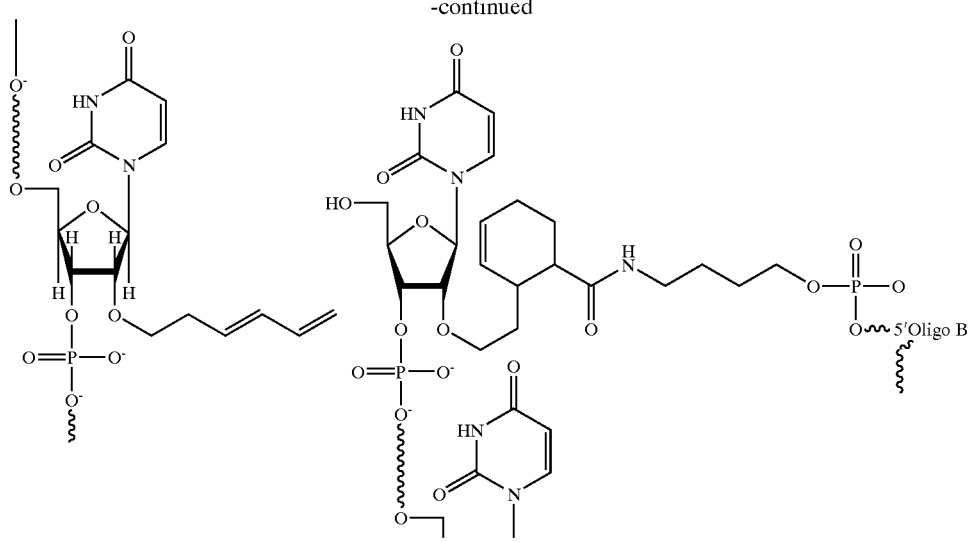
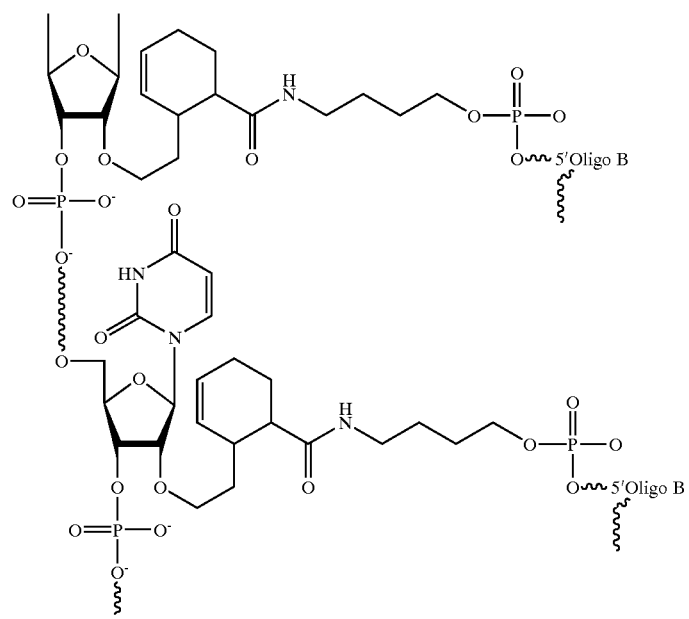
Scheme 22 illustrates the heterodimerization of two oligonucleotides, each of which has only one site of functionalization.
SCHEME 22
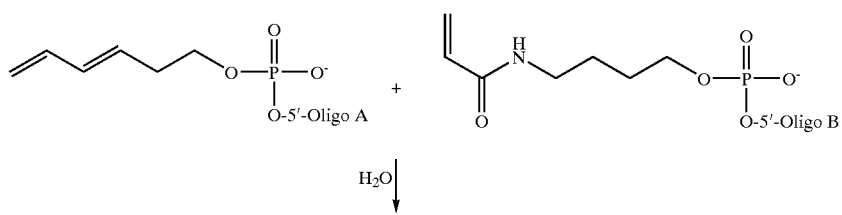

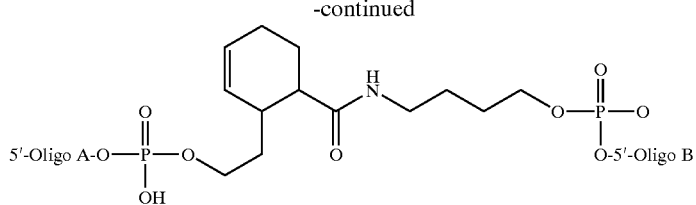

Example 16

Bioconjugation Via an ene Reaction

Synthesis of a 5'-ene phosphoramidite

An ene oligonucleotide is prepared as set forth in Scheme 23.

SCHEME 23

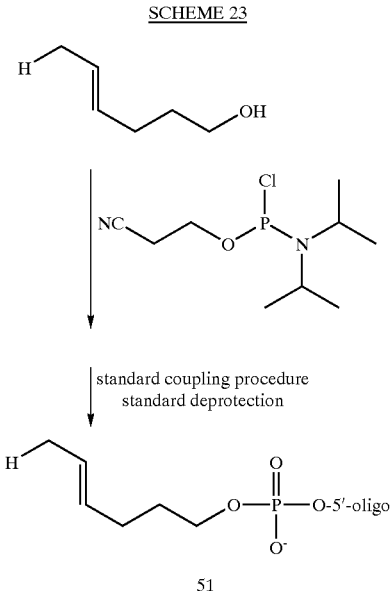

Ene Cycloaddition Reaction

Treatment of ene derivatized oligonucleotide (51) with PEG-maleimide (52) at room temperature in water gives the bioconjugated oligonucleotide (53).

SCHEME 24

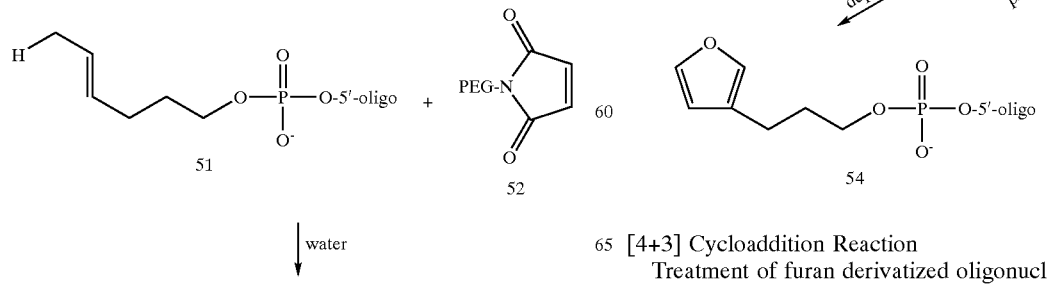

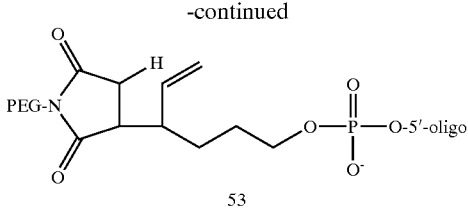

Example 17

Bioconjugation Via [4+3] cycloaddition
Preparation of a Furan Derivatized oligonucleotide
A furan derivatized oligonucleotide is prepared as set forth in Scheme 25.

SCHEME 25

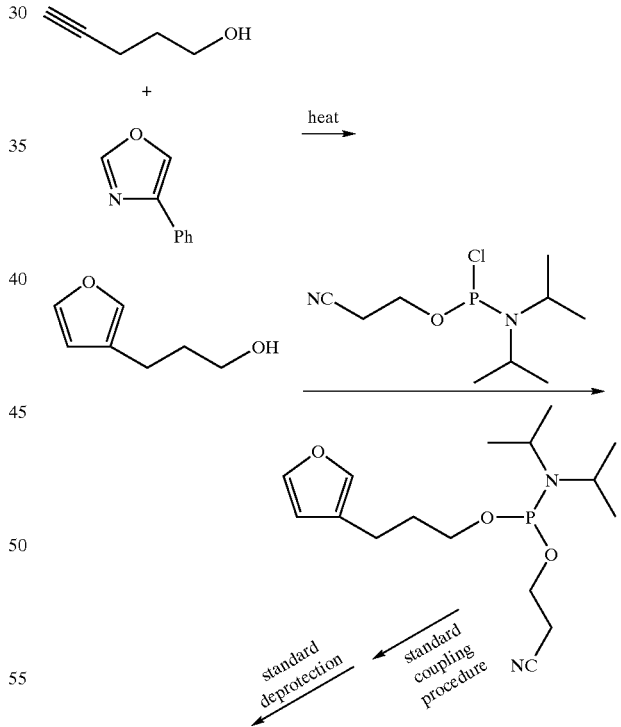

[4+3] Cycloaddition Reaction
Treatment of furan derivatized oligonucleotide (54) with compound (55) at room temperature in water and triethylamine gives the derivatized oligonucleotide (56). (Lubineau (1997) Tetrahedron Lett. 38:8031).

SCHEME 26

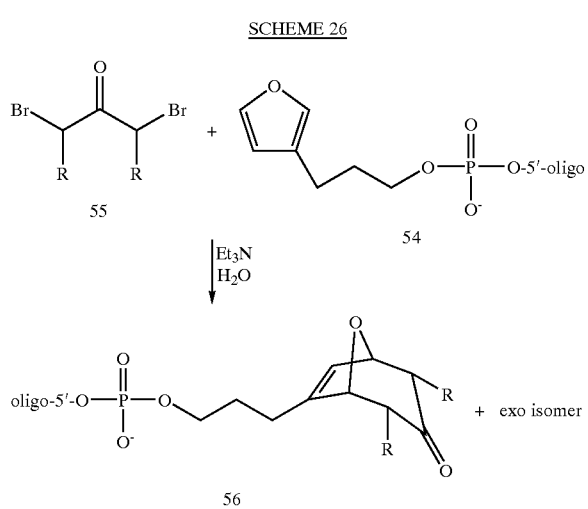

Example 18

Application of Bioconjugation to the Production of Prodrug Libraries

Schemes 27 and 28 illustrate the application of the method of this invention to the production of prodrug libraries.

SCHEME 27

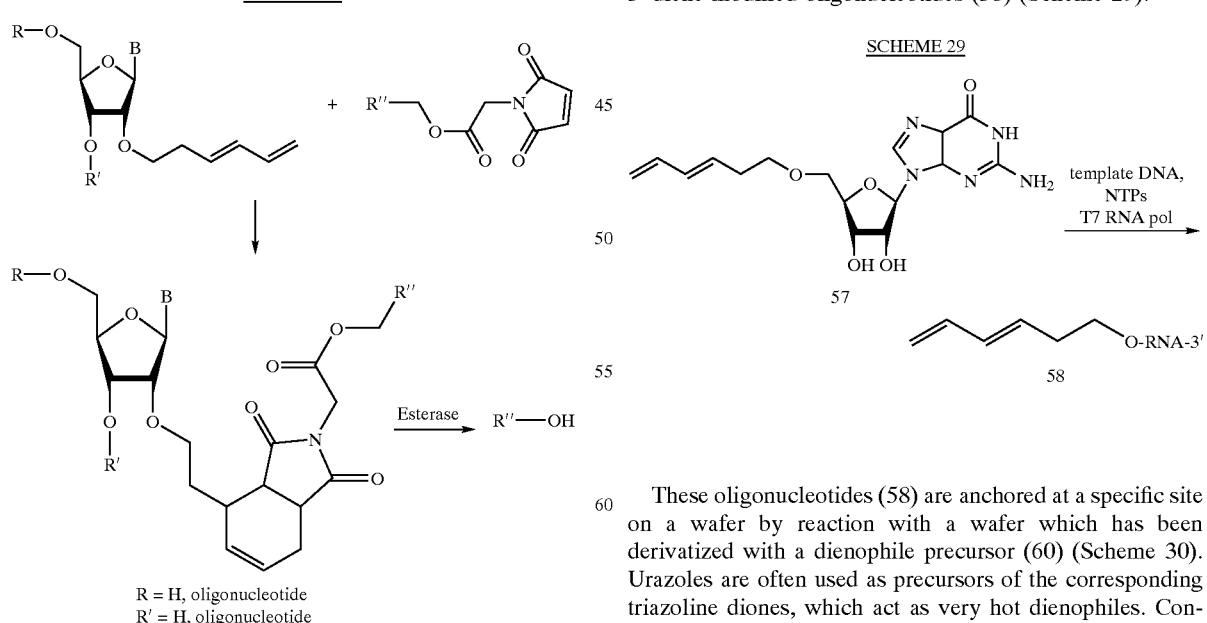

SCHEME 28

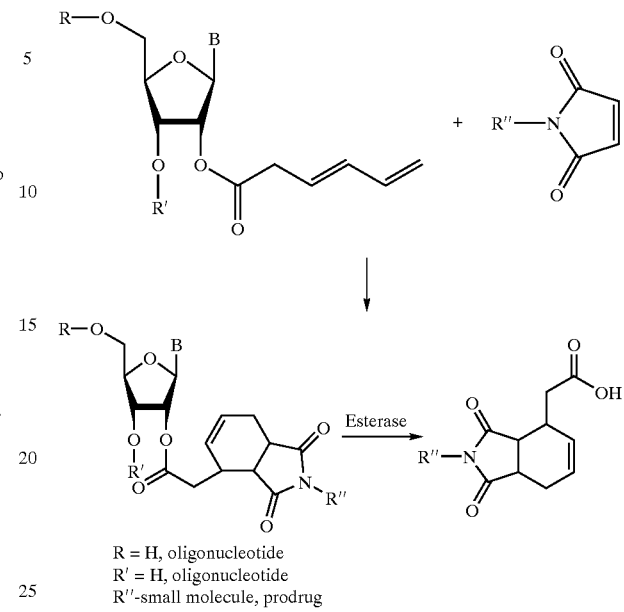

R = H, oligonucleotide
R' = H, oligonucleotide
R''-small molecule, prodrug

Example 19

5'-Diene Bearing Transcripts for Conjugation to Detectors, Resins, or Chips

The polymerization of RNA by T7 RNA polymerase is initiated with 5'-(3,5-hexadiene)guanosine (57) to give 5'-diene modified oligonucleotides (58) (Scheme 29).

SCHEME 29

These oligonucleotides (58) are anchored at a specific site on a wafer by reaction with a wafer which has been derivatized with a dienophile precursor (60) (Scheme 30). Urazoles are often used as precursors of the corresponding triazoline diones, which act as very hot dienophiles. Conversion of urazoles to triazoline diones is achieved by oxidation with oxidants such as tert-butyl hypochlorite, but may also be achieved by photooxidation.

SCHEME 30 no reaction with
diene-oligonucleotide

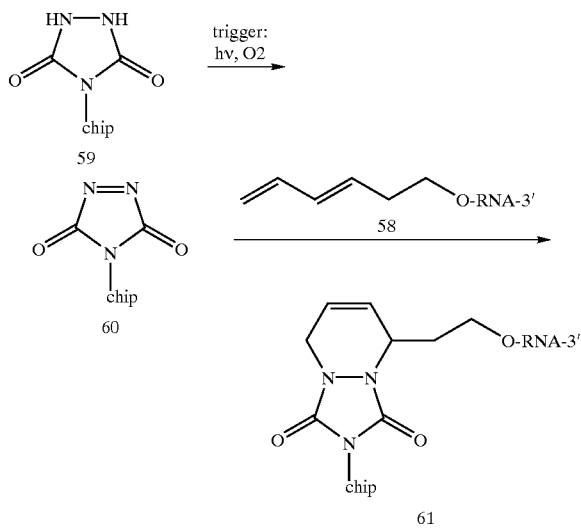

What is claimed is:

1. A method for bioconjugating macromolecules comprising the step of reacting a macromolecule derivatized with a moiety capable of undergoing a cycloaddition reaction, wherein said macromolecule is selected from the group consisting of nucleic acids, oligonucleotides, proteins, peptides, carbohydrates, polysaccharides, glycoproteins, lipids, hormones, drugs and prodrugs with a molecular entity derivatized with a moiety capable of reacting with said derivatized macromolecule via a cycloaddition reaction, wherein said derivatized macromolecule and said derivatized molecular entity are unassociated.

2. The method of claim 1 wherein said cycloaddition reaction is selected from the group consisting of a Diels-Alder reaction, a 1,3-dipolar cycloaddition, a [2+2] cycloaddition, reaction, a ketene cycloaddition and an ene cycloaddition reaction.

3. The method of claim 1 wherein said molecular entity is selected from the group consisting of a macromolecule, antibody, polymer, resin, non-immunogenic high molecular weight compound and a diagnostic detector molecule.

4. The method of claim 3 wherein said diagnostic detector molecule is selected from the group consisting of fluorescent, chemiluminescent, radioisotope and bioluminescent marker compounds and biotin.

5. The method of claim 3 wherein said diagnostic detector molecule is selected from the group consisting of a dienophile derivatized fluorescein, coumarin and a metal chelator.

6. The method of claim 5 wherein said dienophile is a maleimide.

7. The method of claim 3 wherein said polymer is selected from polyethylene glycol or polystyrene.

8. The method of claim 1 wherein said macromolecule is derivatized with a moiety selected from the group consisting of a diene, dienophile and 1,3-dipolarophile.

9. The method of claim 1 wherein said molecular entity is derivatized with a group selected from the group consisting of a diene, dienophile and 1,3-dipolarophile.

10. The method of claim 1 wherein said derivatized macromolecule is an oligonucleotide.

11. The method of claim 10 wherein said derivatized oligonucleotide is selected from the group of compounds having the following structure

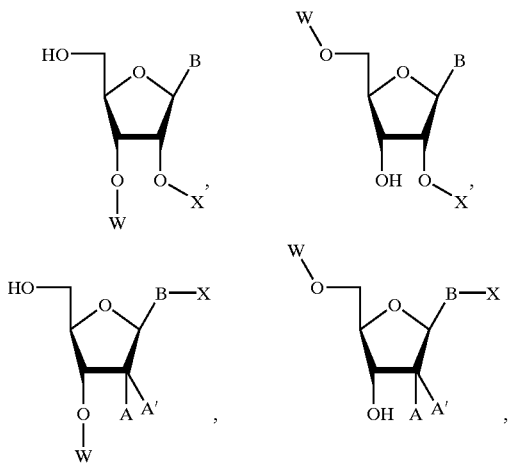

-continued

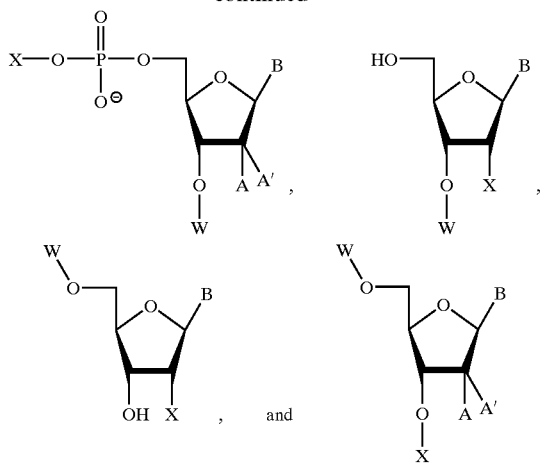

wherein
B is a nucleobase;
A and A' are 2'-sugar substituents;
W is independently selected from the group consisting of a nucleotide or an oligonucleotide having between 2–1000 nucleobases; and
X is a diene, dienophile, 1,3-dipolarophile, 1,3-dipole or other moiety capable of undergoing a cycloaddition reaction additionally, when X is attached to the nucleobase B it can be attached to a carbon atom, an exocyclic nitrogen or an exocyclic oxygen.

12. The method of claim 11 wherein
A and A' are independently selected from the group consisting of H, $^2$H, $^3$H, Cl, F, OH, $NHOR^1$, $NHOR^3$, $NHNHR^3$, $NHR^3$, =NH, CHCN, $CHCl_2$, SH, $SR^3$, $CFH_2$, $CF_2H$, $CR^2{}_2Br$, $-(OCH_2CH_2)_nOCH_3$, $OR^4$ and imidazole;
$R^1$ is selected from the group consisting of H and an alcohol protecting group;
$R^2$ is selected from the group consisting of =O, =S, H, OH, $CCl_3$, $CF_3$, halide, optionally substituted $C_1$–$C_{20}$ alkyl (including cyclic, straight chain, and branched), alkenyl, aryl, $C_1$–$C_{20}$ acyl, benzoyl, $OR^4$ and esters;
$R^3$ is selected from the group consisting of $R^2$, $R^4$, CN, $C(O)NH_2$, $C(S)NH_2$, $C(O)CF_3$, $SO_2R^4$, amino acid, peptide and mixtures thereof;
$R^4$ is selected from the group consisting of an optionally substituted hydrocarbon ($C_1$–$C_{20}$ alkyl, $C_2$–$C_{20}$ alkenyl, $C_2$–$C_{20}$ alkynyl), an optionally substituted heterocycle, t-butyldimethylsilyl ether, triisopropylsilyl ether, nucleoside, carbohydrate, fluorescent label and phosphate; and
X is selected from the group consisting of an alkyl or substituted alkyl group bearing a conjugated diene unit, an alkoxy or substituted alkoxy group bearing a conjugated diene unit, $CH_2$=CHCH=$CHCH_2CH_2O$—, maleimide substituted alkoxy groups, dienophile substituted alkoxy groups, alkoxy groups, an alkylamino or substituted alkylamino group bearing a conjugated diene unit, maleimide substituted alkylamino groups or substituted alkylamino groups, an alkylamino group or substituted alkylamino group bearing a dienophile moiety.

13. The method of claim 12 wherein A is selected from the group consisting of H, OH, $NH_2$, Cl, F, $NHOR^3$, $OR^4$ and $OSiR^4{}_3$.

14. The method of claim 1 wherein said cycloaddition reaction is a Diels-Alder reaction.

15. A compound selected from the group of compounds having the following structure:

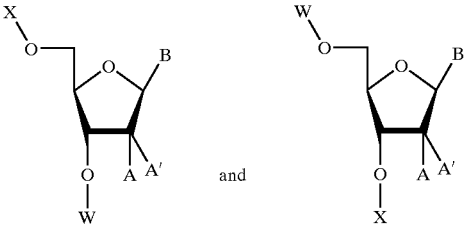

wherein
B is a nucleobase;
A and A' are 2'-sugar substituents;
W is independently selected from the group consisting of a nucleotide, an oligonucleotide having between 2–1000 nucleobases, or H; and
X is a diene, dienophile, 1,3-dipolarophile, 1,3-dipole or other moiety capable of undergoing a cycloaddition reaction additionally, when X is attached to the nucleobase B it can be attached to a carbon atom, an exocyclic nitrogen or an exocyclic oxygen.

16. The compound of claim 15 wherein
A and A' are independently selected from the group consisting of H, $^2$H, $^3$H, Cl, F, OH, $NHOR^1$, $NHOR^3$, $NHNHR^3$, $NHR^3$, =NH, CHCN, $CHCl_2$, SH, $SR^3$, CFH2, $CF_2H$, $CR^2{}_2Br$, $-(OCH_2CH_2)_nOCH_3$, $OR^4$ and imidazole;
$R^1$ is selected from the group consisting of H and an alcohol protecting group;
$R^2$ is selected from the group consisting of =O, =S, H, OH, $CCl_3$, $CF_3$, halide, optionally substituted C1–C20 alkyl (including cyclic, straight chain, and branched), alkenyl, aryl, C1–C20 acyl, benzoyl, $OR^4$ and esters;
$R^3$ is selected from the group consisting of $R^2$, $R^4$, CN, $C(O)NH_2$, $C(S)NH_2$, $C(O)CF_3$, $SO_2R^4$, amino acid, peptide and mixtures thereof;
$R^4$ is selected from the group consisting of an optionally substituted hydrocarbon (C1–C20 alkyl, C2–C20 alkenyl, C2–C20 alkynyl), an optionally substituted heterocycle, t-butyldimethylsilyl ether, triisopropylsilyl ether, nucleoside, carbohydrate, fluorescent label and phosphate; and
X is selected from the group consisting of an alkyl or substituted alkyl group bearing a conjugated diene unit, an alkoxy or substituted alkoxy group bearing a conjugated diene unit, $CH_2$=CHCH=$CHCH_2CH_2O$—, maleimide substituted alkoxy groups, dienophile substituted alkoxy groups, alkoxy groups, an alkylamino or substituted alkylamino group bearing a conjugated diene unit, maleimide substituted alkylamino groups or substituted alkylamino groups, an alkylamino group or substituted alkylamino group bearing a dienophile moiety.

17. The compound of claim 16 wherein A is selected from the group consisting of H, OH, $NH_2$, Cl, F, $NHOR^3$, $OR^4$ and $OSiR^4{}_3$.

18. A derivatized oligonucleotide selected from the group consisting of:
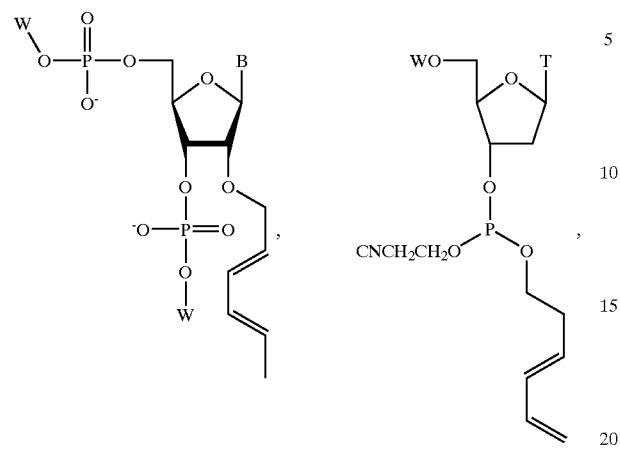
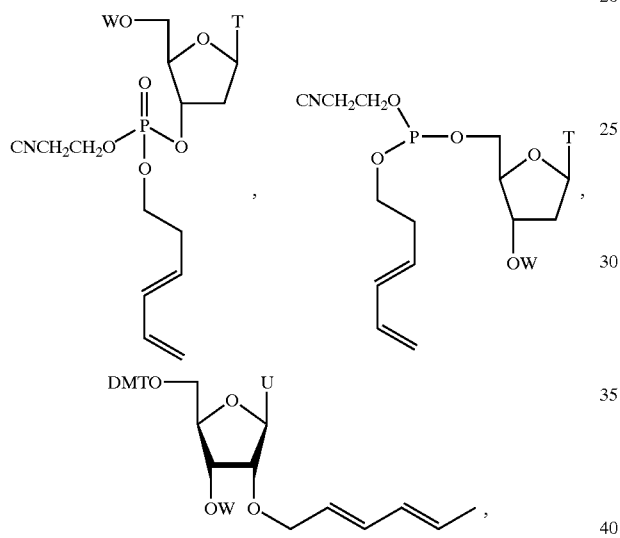
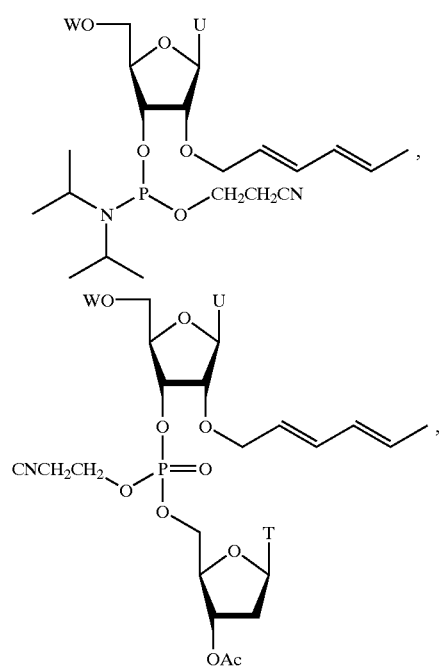
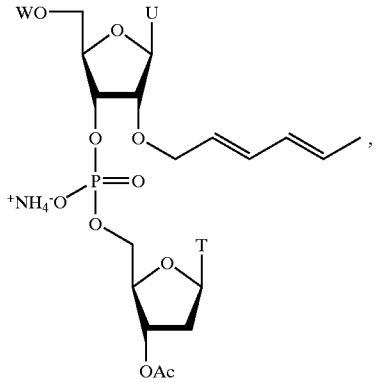
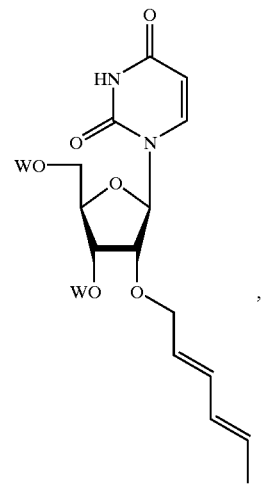
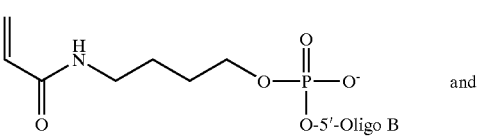
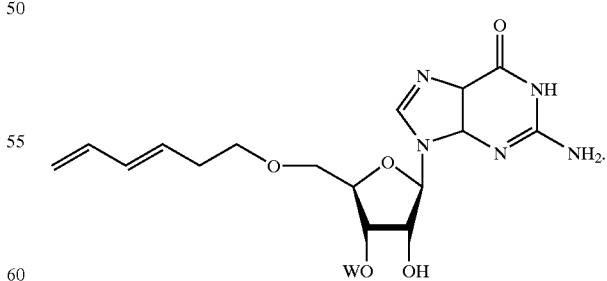
wherein W is independently selected from a nucleotide or an oligonucleotide having between 2–1000 nucleobases.

19. A compound selected from the group consisting of:
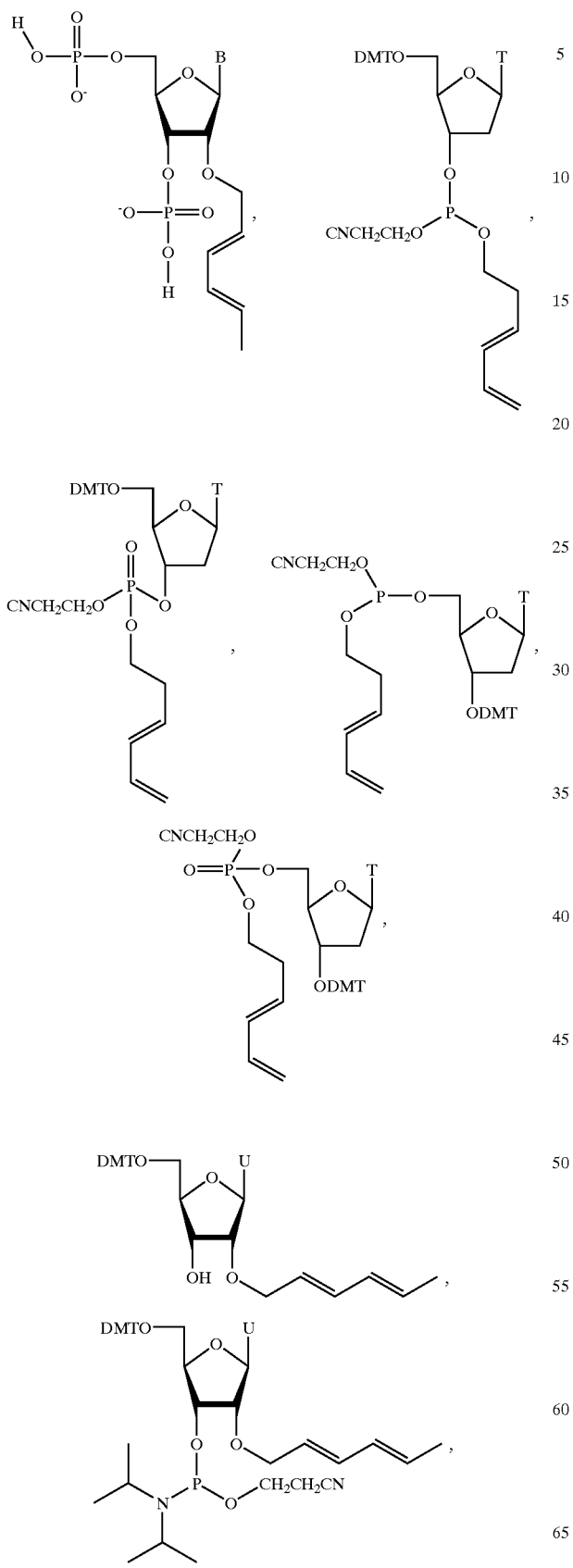
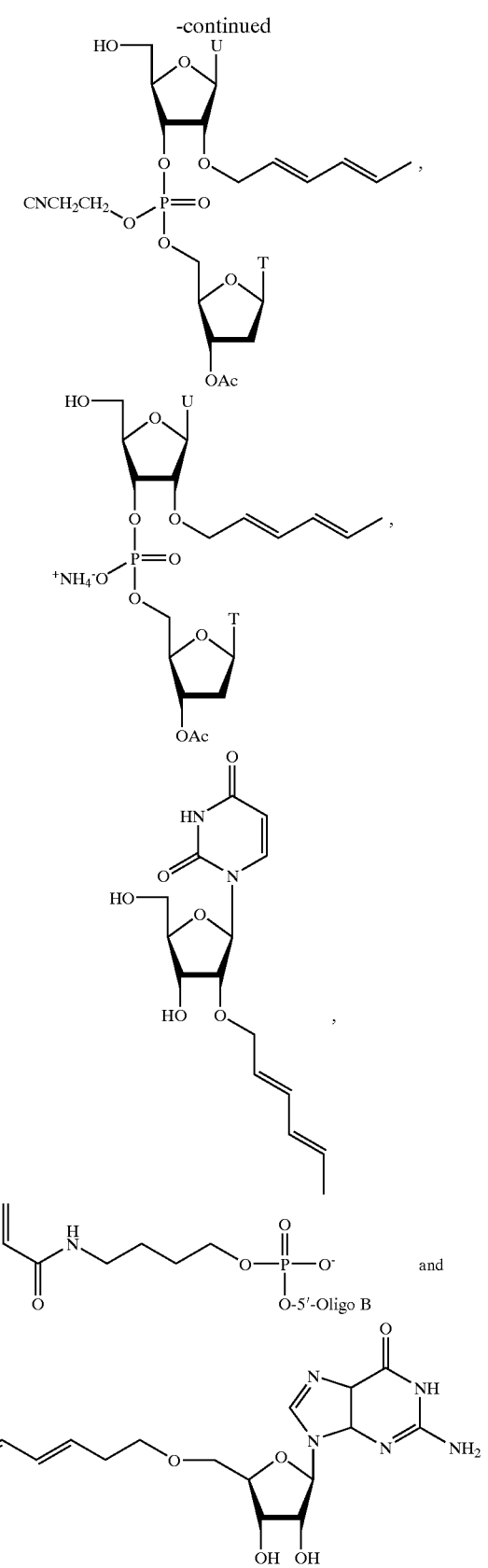
wherein
B is a nucleobase.
* * * * *